United States Patent
Schenk et al.

(10) Patent No.: US 8,741,298 B2
(45) Date of Patent: *Jun. 3, 2014

(54) APOE IMMUNOTHERAPY

(75) Inventors: Dale B. Schenk, Hillsborough, CA (US);
Tarlochan S. Nijjar, Orinda, CA (US);
Philip W. Payne, Sunnyvale, CA (US);
Robin Barbour, Walnut Creek, CA (US)

(73) Assignee: Neotope Biosciences Limited (IE)

(*) Notice: Subject to any disclaimer, the term of this patent is extended or adjusted under 35 U.S.C. 154(b) by 0 days.

This patent is subject to a terminal disclaimer.

(21) Appl. No.: 13/368,260

(22) Filed: Feb. 7, 2012

(65) Prior Publication Data

US 2012/0204275 A1    Aug. 9, 2012

Related U.S. Application Data

(63) Continuation of application No. 61/440,284, filed on Feb. 7, 2011.

(51) Int. Cl.
*A61K 39/395* (2006.01)
*C07K 16/18* (2006.01)
*C07K 4/12* (2006.01)
*C12N 5/06* (2006.01)
*C12N 15/74* (2006.01)
*C12N 15/81* (2006.01)

(52) U.S. Cl.
USPC ............... 424/145.1; 424/158.1; 424/184.1; 530/300; 530/387.3; 530/388.15; 530/388.25; 536/23.53

(58) Field of Classification Search
None
See application file for complete search history.

(56) References Cited

U.S. PATENT DOCUMENTS

| | | |
|---|---|---|
| 2003/0099655 A1 | 5/2003 | Watkins et al. |
| 2004/0157267 A1 | 8/2004 | Huang |
| 2005/0084906 A1 | 4/2005 | Goetsch et al. |
| 2005/0176021 A1 | 8/2005 | Gu et al. |
| 2005/0281828 A1 | 12/2005 | Bowdish et al. |
| 2007/0104715 A1 | 5/2007 | Nordstedt et al. |
| 2008/0044406 A1 | 2/2008 | Johnson-Wood et al. |
| 2008/0090998 A1 | 4/2008 | Abad et al. |
| 2008/0292639 A1 | 11/2008 | Shen et al. |
| 2009/0022728 A1 | 1/2009 | Lin |
| 2009/0042783 A1 | 2/2009 | Vitek et al. |
| 2009/0082271 A1 | 3/2009 | Mahley et al. |
| 2009/0280116 A1 | 11/2009 | Smith et al. |
| 2010/0260748 A1 | 10/2010 | Elkins et al. |

FOREIGN PATENT DOCUMENTS

WO    WO 2009/150295 A1    12/2009

OTHER PUBLICATIONS

Wu et al., Monoclonal Antibody-mediated Inhibition of HIV—1 Reverse Transcriptase Polymerase Activity. The Journl of Biological Chemistry, Val. 268, No. 14, Issue of May 15, pp. 9980-9985,1993.*

(Continued)

*Primary Examiner* — Jeffrey Stucker
*Assistant Examiner* — Aurora M Fontainhas
(74) *Attorney, Agent, or Firm* — Alston & Bird LLP

(57) ABSTRACT

The present invention provides antibodies that preferentially bind to an ApoE(1-272) fragment relative to ApoE(1-299). These antibodies serve to reduce the toxicity of this fragment and find use in treatment and prophylaxis of a variety of neurological diseases.

65 Claims, 6 Drawing Sheets

15G8 VH alignment

| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| m15G8VH | E | V | K | L | V | E | S | G | G | G | L | V | K | P | G | G | S | L | K | L |
| AAX82494VH | Q | V | Q | L | Q | E | S | G | G | G | L | V | K | P | G | G | S | L | K | L |
| Hu15G8VHv1 | E | V | K | L | V | E | S | G | G | G | L | V | K | P | G | G | S | L | K | L |
| Hu15G8VHv2 | Q | V | Q | L | Q | E | S | G | G | G | L | V | K | P | G | G | S | L | K | L |

| Kabat Numbering | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| m15G8VH | S | C | A | A | S | G | F | T | F | S | *F* | *Y* | *A* | *M* | *S* | W | V | R | Q | T |
| AAX82494VH | S | C | A | A | S | G | F | T | F | S | *S* | *Y* | *G* | *M* | *S* | W | V | R | Q | T |
| Hu15G8VHv1 | S | C | A | A | S | G | F | T | F | S | *F* | *Y* | *A* | *M* | *S* | W | V | R | Q | T |
| Hu15G8VHv2 | S | C | A | A | S | G | F | T | F | S | *F* | *Y* | *A* | *M* | *S* | W | V | R | Q | T |

| Kabat Numbering | 41 | 42 | 43 | 44 | 45 | 46 | 47 | 48 | 49 | 50 | 51 | 52 | 52A | 53 | 54 | 55 | 56 | 57 | 58 | 59 |
|---|---|---|---|---|---|---|---|---|---|---|---|---|---|---|---|---|---|---|---|---|
| m15G8VH | P | E | K | R | L | E | W | V | A | *S* | *L* | *S* | *-* | *R* | *G* | *G* | *S* | *T* | *Y* | *Y* |
| AAX82494VH | P | D | K | R | L | E | W | V | A | *T* | *I* | *S* | *S* | *G* | *G* | *S* | *Y* | *T* | *Y* | *Y* |
| Hu15G8VHv1 | P | E | K | R | L | E | W | V | A | *S* | *L* | *S* | *-* | *R* | *G* | *G* | *S* | *T* | *Y* | *Y* |
| Hu15G8VHv2 | P | D | K | R | L | E | W | V | A | *S* | *L* | *S* | *-* | *R* | *G* | *G* | *S* | *T* | *Y* | *Y* |

| Kabat Numbering | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|
| m15G8VH | *P* | *D* | *S* | *V* | *K* | *G* | R | F | T | I | S | R | D | N | A | R | N | T | L | Y |
| AAX82494VH | *P* | *D* | *S* | *V* | *K* | *G* | R | F | T | I | S | R | D | N | A | K | N | T | L | Y |
| Hu15G8VHv1 | *P* | *D* | *S* | *V* | *K* | *G* | R | F | T | I | S | R | D | N | A | K | N | T | L | Y |
| Hu15G8VHv2 | *P* | *D* | *S* | *V* | *K* | *G* | R | F | T | I | S | R | D | N | A | K | N | T | L | Y |

(56) References Cited

OTHER PUBLICATIONS

AvanGens, AvantGen's Antibody Humanization and Discovery Technologies, AvantGen Inc. Technologies and Service Information Jul. 27, 2009 (online) (Retrieved on Jul. 22, 2012) Retrieved from the Internet <URL: http://www.avantgen.com/AvantGensTechnologiesandServices.pdf>.

Dyrberg et al., "Peptides as Antigens Importance of Orientation", *J. Exp. Med*, vol. 164, Oct. 1986, pp. 1344-1349.

Johnson et al., "Kabat Database and its applications: 30 years after the first variability plot", *Nucleic Acids Res.*, vol. 28(1), pp. 214-218, Jan. 2000.

Jost et al., "Mannalian Expression and Secretion of Functional Single-chain Fv Molecules", *Journal of Biological Chemistry*, vol. 269, No. 42, Issue of Oct. 21, pp. 26267-26273 (1994).

Kipriyanov et al., "Generation and Production of Engineered Antibodies" *Molecular Biotechnology*, vol. 26 (2004) p. 39-60.

Mann et al., "Independent effects of APOE on cholesterol metabolism and brain Ab levels in an Alzheimer disease mouse model", *Hum Mol Genet.*, vol. 12(17), p. 1959-1968 (2004).

Nakamura et al., "Apolipoprotein E4 (1-272) fragment is associated with mitochondrial proteins and affects mitochondrial function in neuronal cells" *Molecular Neurodegeneraton*,(Aug. 20, 2009) 4:35 p. 1-11.

PCT/US2012/024195 International Search Report mailed Aug. 3, 2012.

PCT/US2012/024195 Invitation to Pay Additional Fees and, Where Applicable, Protest Fees, mailed May 11, 2012.

PCT/US2012/024195 Written Opinion of the International Searching Authority mailed Aug. 3, 2012.

PIR_538808, Ig heavy chain—mouse, Jan. 21, 2000 (online) [Retrieved on Feb. 6, 2013] Retrieved from the Internet: <URL: http://www.ncbi.nlm.nih.gov/protein/S38808>.

Chang et al., "Lipid- and receptor-binding regions of apolipoprotein E4 fragments act in concert to cause mitochondrial dysfunction and neurotoxicity," *PNAS*, 102(51): 18694-18699 (2005).

Li et al., "Current Therapeutic Antibody Production and Process Optimization," *BioProcessing Journal*, 4(5): 1-8 (2005).

Mahley et al., "Apolipoprotein E4: A causative factor and therapeutic target in neuropathology, including Alzheimer's Disease," *PNAS*, 103(15): 5644-5651 (2006).

Rall et al., "Human Apolipoprotein E," *J. Biol. Chem.*, 257(8): 4171-4178 (1982).

Zhong et al., "Understanding the Association of Apolipoprotein E4 with Alzheimer Disease: Clues from Its Structure," *J. Biol. Chem.*, 284(10): 6027-6031 (2009).

\* cited by examiner

Fig. 1

15G8 VH alignment

| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| m15G8VH | E | V | K | L | V | E | S | G | G | G | L | V | K | P | G | G | S | L | K | L |
| AAX82494VH | Q | V | Q | L | Q | E | S | G | G | G | L | V | Q | P | G | G | S | L | K | L |
| Hu15G8VHv1 | E | V | K | L | V | E | S | G | G | G | L | V | K | P | G | G | S | L | K | L |
| Hu15G8VHv2 | Q | V | Q | L | Q | E | S | G | G | G | L | V | Q | P | G | G | S | L | K | L |

| Kabat Numbering | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| m15G8VH | S | C | A | A | S | G | F | T | F | S | *F* | *Y* | *A* | *M* | *S* | W | V | R | Q | T |
| AAX82494VH | S | C | A | A | S | G | F | T | F | S | *S* | *Y* | *G* | *M* | *S* | W | V | R | Q | T |
| Hu15G8VHv1 | S | C | A | A | S | G | F | T | F | S | *F* | *Y* | *A* | *M* | *S* | W | V | R | Q | T |
| Hu15G8VHv2 | S | C | A | A | S | G | F | T | F | S | *F* | *Y* | *A* | *M* | *S* | W | V | R | Q | T |

| Kabat Numbering | 41 | 42 | 43 | 44 | 45 | 46 | 47 | 48 | 49 | 50 | 51 | 52 | 52A | 53 | 54 | 55 | 56 | 57 | 58 | 59 |
|---|---|---|---|---|---|---|---|---|---|---|---|---|---|---|---|---|---|---|---|---|
| m15G8VH | P | E | K | R | L | E | W | V | A | *S* | *L* | *S* | - | *R* | G | *G* | *S* | *T* | *Y* | *Y* |
| AAX82494VH | P | D | K | R | L | E | W | V | A | *T* | *I* | *S* | *S* | *G* | G | *S* | *Y* | *T* | *Y* | *Y* |
| Hu15G8VHv1 | P | E | K | R | L | E | W | V | A | *S* | *L* | *S* | - | *R* | G | *G* | *S* | *T* | *Y* | *Y* |
| Hu15G8VHv2 | P | D | K | R | L | E | W | V | A | *S* | *L* | *S* | - | *R* | G | *G* | *S* | *T* | *Y* | *Y* |

| Kabat Numbering | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|
| m15G8VH | *P* | *D* | *S* | *V* | *K* | *G* | R | F | T | I | S | R | D | N | A | R | N | T | L | Y |
| AAX82494VH | *P* | *D* | *S* | *V* | *K* | *G* | R | F | T | I | S | R | D | N | A | K | N | T | L | Y |
| Hu15G8VHv1 | *P* | *D* | *S* | *V* | *K* | *G* | R | F | T | I | S | R | D | N | A | K | N | T | L | Y |
| Hu15G8VHv2 | *P* | *D* | *S* | *V* | *K* | *G* | R | F | T | I | S | R | D | N | A | K | N | T | L | Y |

Fig. 1 (cont.)

15G8 VH alignment

| Kabat Numbering | 80 | 81 | 82 | 82A | 82B | 82C | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|
| m15G8VH    | L | Q | M | S | S | L | R | S | E | D | T | A | M | F | Y | C | A | R | *E* | *G* |
| AAX82494VH | L | Q | M | S | S | L | K | S | E | D | T | A | M | Y | Y | C | A | R | *L* | *Y* |
| Hu15G8VHv1 | L | Q | M | S | S | L | R | S | E | D | T | A | M | Y | Y | C | A | R | *E* | *G* |
| Hu15G8VHv2 | L | Q | M | S | S | L | K | S | E | D | T | A | M | Y | Y | C | A | R | *E* | *G* |

| Kabat Numbering | 97 | 98 | 99 | 100 | 100A | 100B | 100C | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|
| m15G8VH    | *A* | *T* | *A* | *Y* | *L* | *Y* | *A* | *M* | *D* | *Y* | W | G | Q | G | T | S | V | T | R | S | S |
| AAX82494VH | *Y* | *G* | *Y* | *R* | *Y* | *A* | *M* | *F* | *D* | *Y* | W | G | Q | G | T | M | V | T | V | S | S |
| Hu15G8VHv1 | *A* | *T* | *A* | *Y* | *L* | *Y* | *A* | *M* | *D* | *Y* | W | G | Q | G | T | M | V | T | V | S | S |
| Hu15G8VHv2 | *A* | *T* | *A* | *Y* | *L* | *Y* | *A* | *M* | *D* | *Y* | W | G | Q | G | T | M | V | T | V | S | S |

Fig. 2

15G8 VL alignment

| Kabat Numbering | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| m15G8VL | D | V | L | M | T | Q | T | P | L | S | L | P | V | S | L | G | D | Q | Q | S |
| AAT86035VL | D | V | V | M | T | Q | S | P | L | S | L | P | V | T | L | G | Q | P | A | S |
| Hu15G8VLv1 | D | V | L | M | T | Q | S | P | L | S | L | P | V | T | L | G | Q | P | A | S |
| Hu15G8VLv2 | D | V | V | M | T | Q | S | P | L | S | L | P | V | T | L | G | Q | P | A | S |

| Kabat Numbering | 21 | 22 | 23 | 24 | 25 | 26 | 27 | 27A | 27B | 27C | 27D | 27E | 28 | 29 | 30 | 31 | 32 | 33 | 34 | 35 |
|---|---|---|---|---|---|---|---|---|---|---|---|---|---|---|---|---|---|---|---|---|
| m15G8VL | H | S | C | R | S | S | Q | S | I | V | H | S | N | G | N | T | Y | L | Q | W |
| AAT86035VL | H | S | C | R | S | S | Q | S | L | L | H | S | D | G | N | T | Y | L | L | W |
| Hu15G8VLv1 | H | S | C | R | S | S | Q | S | I | V | H | S | N | G | N | T | Y | L | Q | W |
| Hu15G8VLv2 | H | S | C | R | S | S | Q | S | I | V | H | S | N | G | N | T | Y | L | Q | W |

| Kabat Numbering | 36 | 37 | 38 | 39 | 40 | 41 | 42 | 43 | 44 | 45 | 46 | 47 | 48 | 49 | 50 | 51 | 52 | 53 | 54 | 55 |
|---|---|---|---|---|---|---|---|---|---|---|---|---|---|---|---|---|---|---|---|---|
| m15G8VL | Y | L | Q | K | P | G | Q | S | P | K | L | L | I | Y | K | V | S | N | R | F |
| AAT86035VL | F | L | Q | R | P | G | Q | S | P | R | R | L | L | Y | K | V | S | D | R | D |
| Hu15G8VLv1 | Y | L | Q | R | P | G | Q | S | P | R | L | L | I | Y | K | V | S | N | R | F |
| Hu15G8VLv2 | F | L | Q | R | P | G | Q | S | P | R | R | L | L | Y | K | V | S | N | R | F |

| Kabat Numbering | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|
| m15G8VL | S | G | V | P | D | R | F | S | G | S | G | S | G | T | D | F | T | L | K | I |
| AAT86035VL | S | G | V | P | D | R | F | S | G | S | G | S | G | T | D | F | T | L | K | I |
| Hu15G8VLv1 | S | G | V | P | D | R | F | S | G | S | G | S | G | T | D | F | T | L | K | I |
| Hu15G8VLv2 | S | G | V | P | D | R | F | S | G | S | G | S | G | T | D | F | T | L | K | I |

Fig. 2 (cont.)

15G8 VL alignment

| Kabat Numbering | 76 | 77 | 78 | 79 | 80 | 81 | 82 | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|---|
| m15G8VL    | S | R | V | E | A | E | D | L | G | I | Y | Y | C | *F* | *Q* | *G* | *S* | *H* | *V* | *P* |
| AAT86035VL | S | R | V | E | A | E | D | V | G | V | Y | Y | C | *M* | *Q* | *G* | *T* | *H* | *W* | *P* |
| Hu15G8VLv1 | S | R | V | E | A | E | D | V | G | V | Y | Y | C | *F* | *Q* | *G* | *S* | *H* | *V* | *P* |
| Hu15G8VLv2 | S | R | V | E | A | E | D | V | G | V | Y | Y | C | *F* | *Q* | *G* | *S* | *H* | *V* | *P* |

| Kabat Numbering | 96 | 97 | 98 | 99 | 100 | 101 | 102 | 103 | 104 | 105 | 106 | 107 |
|---|---|---|---|---|---|---|---|---|---|---|---|---|
| m15G8VL    | *W* | *T* | F | G | G | G | T | K | L | E | I | K |
| AAT86035VL | *W* | *T* | F | G | Q | G | T | K | V | E | I | K |
| Hu15G8VLv1 | *W* | *T* | F | G | Q | G | T | K | V | E | I | K |
| Hu15G8VLv2 | *W* | *T* | F | G | Q | G | T | K | V | E | I | K |

Fig. 4

APOE IMMUNOTHERAPY

CROSS-REFERENCE TO RELATED APPLICATION

This application claims priority to U.S. Provisional Patent Application No. 61/440,284, filed Feb. 7, 2011, the contents of which are incorporated by reference in the entirety.

REFERENCE TO A SEQUENCE LISTING

The Sequence Listing written in file Sequence_Listing_for_057450-414811.txt is 41,971 bytes and was created on Feb. 7, 2012. The information contained in this file is hereby incorporated by reference.

BACKGROUND OF THE INVENTION

Apolipoprotein E (ApoE), which maps to 19q13.2, encodes a protein with a role in lipid transport and cholesterol processing. The protein has an N-terminal domain (residues 1-191) containing a low density lipoprotein receptor binding sites, a C-terminal domain (residues 216-299) containing the major lipid binding sites (residues 240-272) and a hinge region between the two domains.

The ApoE gene has three allelic variants: ApoE4, ApoE3, and ApoE2. ApoE3 (also referred to herein as "E4," E3," and "E2," respectively) is the most common form and ApoE2 is the least common. The frequency of the ApoE4 version of the gene in different populations varies, but is always less than 30% and frequently 8%-15%. ApoE4 is known to be a strong risk factor for Alzheimer's disease (AD). The presence of one copy of the allele increases the likelihood of acquiring the disease about threefold and increases the onset of disease an average of 5 years. Two copies of the same allele increases the risk of AD about 8-fold and decreases the age of onset by an average of 10 years. Analysis of autopsies from individuals who have died with AD and have an ApoE4 allele show that Aβ-related pathologies such as plaques and cerebrovascular amyloid is generally increased in those individuals carrying the allele. ApoE as a lipoprotein interacts with lipid particles and hence is involved in lipid transport in plasma, particularly cholesterol. It has been reported to have a role in the maintenance and repair of neurons. The association between ApoE4 and Alzheimer's disease may be mediated by multiple mechanisms both Aβ-dependent and independent. ApoE4 has reported to be associated with increased production and deposition of Aβ and itself to form toxic aggregates and proteolytic fragments (Zhong et al., J. Biol. Chem. 284, 6027-6031 (2009); Mahley et al., PNAS 103, 5644-5651 (2006)).

The E2, E3 and E4 isoforms each has differential capacity to transport lipids and has differential effects on AD with E4 increasing and E2 decreasing the overall risk of AD. The three alleles each differ from one another at only two residues in humans, positions 112 and 158. Apo E2 has a Cys at both sites. E3 has a Cys at 112 and Arg at 158, and E4 has an Arg at both sites. These changes result in overall structural differences in all three isoforms that appear to account for the AD disease-causing propensities.

SUMMARY OF THE CLAIMED INVENTION

The invention provides an antibody, e.g., a monoclonal antibody, that preferentially binds to ApoE(1-272) relative to binding to ApoE(1-299). Optionally, the antibody binds to an epitope including residue 272 of ApoE(1-272). Optionally, the antibody binds to an epitope including a free carboxyl group of position 272 of ApoE(1-272). Optionally, the antibody binds to the E4 isoform of ApoE(1-272). The monoclonal antibody can be a humanized, chimeric, veneered or human antibody. The monoclonal antibody can be an Fab fragment, single chain Fv, or single domain antibody. The isotype can be human IgG isotype, for example, IgG1, IgG2, or IgG4. Optionally there is at least one mutation in the constant region.

The invention further provides a monoclonal antibody having the three light chain CDRs as defined by Kabat and three heavy chain CDRs as defined by Kabat of monoclonal antibody 12C12, 15E10 or 15G8. 12C12, 15E10 and 15G8 are mouse antibodies characterized by a light chain variable region of SEQ ID NO:10 and a heavy chain variable region of SEQ ID NO:9.

The invention further provides a monoclonal antibody comprising three light chain CDRs and three heavy chain CDRs, each light chain CDR having at least 90% sequence identity to a corresponding CDR designated as SEQ ID NO:22 (CDRL1), SEQ ID NO:23 (CDR L2), and SEQ ID NO:24 (CDR L3), and each heavy chain CDR having at least 90% sequence identity to a corresponding CDR designated as SEQ ID NO:19 (CDR H1), SEQ ID NO:20 (CDR H2), and SEQ ID NO:21 (CDR H3).

The invention further provides a monoclonal antibody comprising three light chain Kabat CDRs and three heavy chain Kabat CDRs, each CDR differs in sequence from a corresponding CDR from 15G8 by no more than 6 replacements, deletions or insertions, wherein 15G8 is a mouse antibody characterized by a light chain variable region of SEQ ID NO:10 and a heavy chain variable region of SEQ ID NO:9. In some antibodies, each CDR differs in sequence by no more than 1 replacement, deletion or insertion. In some antibodies, each light chain CDR has a 100% sequence identity to a corresponding CDR from 15G8 and no heavy chain CDR differs in sequence by more than 6 replacements, deletions or insertions. In some antibodies, each of light chain CDR L1, L2, L3 and CDR H1 and CDR H3 has a 100% sequence identity to a corresponding CDR from 15G8, and CDR H2 differs in sequence by no more than 6 replacements, deletions or insertions. In some antibodies, the mature heavy chain variable region comprises an amino acid sequence of SEQ ID NO:9 and the mature light chain variable region comprises an amino acid sequence of SEQ ID NO:10.

The invention further provides a monoclonal antibody that competes for specific binding to ApoE with 15G8 or a monoclonal antibody that binds to the same epitope on ApoE as 15G8.

The invention further provides a humanized, chimeric or veneered form of monoclonal antibody 12C12, 15E10 or 15G8. Optionally, the antibody comprises a light chain variable region comprising three light chain Kabat CDRs of SEQ ID NO:18 and a heavy chain variable region comprising three heavy chain CDRs of SEQ ID NO:17. In some antibodies, the light chain variable region framework has at least 85%, 90%, 91%, 92% 93%, 94%, 95%, 96%, 97%, 98%, or 99% sequence identity to AAT86035 (SEQ ID NO:8). In some antibodies, the heavy chain variable region framework has at least 85%, 90%, 91%, 92% 93%, 94%, 95%, 96%, 97%, 98%, or 99% sequence identity to AAX82494 (SEQ ID NO:7).

The invention further provides an antibody comprising a mature heavy chain variable region having at least 85%, 90%, 91%, 92% 93%, 94%, 95%, 96%, 97%, 98%, or 99% sequence identity to SEQ ID NO:17, and/or a mature light chain variable region having at least 85%, 90%, 91%, 92% 93%, 94%, 95%, 96%, 97%, 98%, or 99% sequence identity to SEQ ID NO:18. In some of such antibodies, any differences in CDRs of the mature heavy chain variable region and mature light variable region from SEQ ID NOs. 52 and 60 respectively reside in positions H60-H65. In some such antibodies, the mature heavy chain variable region comprises the three Kabat CDRs of SEQ ID NO:17 and the mature light chain variable region comprises the three Kabat CDRs of SEQ ID NO:18. In some such antibodies, the mature heavy chain variable region has at least 85%, 90%, 91%, 92% 93%, 94%, 95%, 96%, 97%, 98%, or 99% sequence identity to SEQ ID NO:17. In some such antibodies, the mature light chain variable region has at least 85%, 90%, 91%, 92% 93%, 94%, 95%, 96%, 97%, 98%, or 99% sequence identity to SEQ ID NO:18. In some antibodies, position L3 (Kabat numbering) is occupied by L. In some antibodies, position L36 (Kabat numbering) is occupied by Y. In some antibodies, position L46 (Kabat numbering) is occupied by L. In some antibodies, position H1 (Kabat numbering) is occupied by E. In some antibodies, position H3 (Kabat numbering) is occupied by K. In some antibodies, position H5 (Kabat numbering) is occupied by V. In some antibodies, position H42 (Kabat numbering) is occupied by E. In some antibodies, position H83 (Kabat numbering) is occupied by R. In some antibodies, the amino acid sequence of the mature heavy chain variable region is SEQ ID NO:17 and the amino acid sequence of the mature light chain variable region is SEQ ID NO:18 provided that position L3 (Kabat numbering) can be occupied by V or L, position L36 (Kabat numbering) can be occupied by F or Y, position L46 (Kabat numbering) can be occupied by R or L, position H1 (Kabat numbering) can be occupied by Q or E, position H3 (Kabat numbering) can be occupied by Q or K, position H5 (Kabat numbering) can be occupied by Q or V, position H42 (Kabat numbering) can be occupied by D or E, and position H83 (Kabat numbering) can be occupied by K or R. In some such antibodies, position L3 (Kabat numbering) is occupied by L, position L36 (Kabat numbering) is occupied by Y, and position L46 (Kabat numbering) is occupied by L. In some such antibodies, position L3 (Kabat numbering) is occupied by V, position L36 (Kabat numbering) is occupied by F, and position L46 (Kabat numbering) is occupied by R. In some such antibodies, position H1 (Kabat numbering) is occupied by E, position H3 (Kabat numbering) is occupied by K, position H5 (Kabat numbering) is occupied by V, position H42 (Kabat numbering) is occupied by E, and position H83 (Kabat numbering) is occupied by R. In some such antibodies, position H1 (Kabat numbering) is occupied by Q, position H3 (Kabat numbering) is occupied by Q, position H5 (Kabat numbering) is occupied by Q, position H42 (Kabat numbering) is occupied by D, and position H83 (Kabat numbering) is occupied by K.

The invention further provides an antibody comprising a humanized heavy chain comprising the three Kabat CDRs of SEQ ID NO:17 and a humanized light chain comprising the three CDRs of SEQ ID NO:18. In some antibodies, the mature heavy chain variable framework region having 65-85% identity to the corresponding heavy chain variable region framework of SEQ ID NO:17, and the mature light chain variable framework region having 65-85% identity to the corresponding light chain variable region framework of SEQ ID NO:18. Optionally, position L3 (Kabat numbering) is occupied by L, and/or position L36 (Kabat numbering) is occupied by Y, and/or position L46 (Kabat numbering) is occupied by L, and/or position H1 (Kabat numbering) is occupied by E, and/or position H3 (Kabat numbering) is occupied by K, and/or position H5 (Kabat numbering) is occupied by V, and/or position H42 (Kabat numbering) is occupied by E, and/or position H83 (Kabat numbering) is occupied by R. Optionally, position L3 (Kabat numbering) is occupied by V, and/or position L36 (Kabat numbering) is occupied by F, and/or position L46 (Kabat numbering) is occupied by R, and/or position H1 (Kabat numbering) is occupied by Q, and/or position H3 (Kabat numbering) is occupied by Q, and/or position H5 (Kabat numbering) is occupied by Q, and/or position H42 (Kabat numbering) is occupied by D, and/or position H83 (Kabat numbering) is occupied by K. Optionally, position L3 (Kabat numbering) is occupied by L, and/or position L36 (Kabat numbering) is occupied by Y, and/or position L46 (Kabat numbering) is occupied by L, and/or position H1 (Kabat numbering) is occupied by Q, and/or position H3 (Kabat numbering) is occupied by Q, and/or position H5 (Kabat numbering) is occupied by Q, and/or position H42 (Kabat numbering) is occupied by D, and/or position H83 (Kabat numbering) is occupied by K. Optionally, position L3 (Kabat numbering) is occupied by V, and/or position L36 (Kabat numbering) is occupied by F, and/or position L46 (Kabat numbering) is occupied by R, and/or position H1 (Kabat numbering) is occupied by E, and/or position H3 (Kabat numbering) is occupied by K, and/or position H5 (Kabat numbering) is occupied by V, and/or position H42 (Kabat numbering) is occupied by E, and/or position H83 (Kabat numbering) is occupied by R. In some antibodies, position L3 (Kabat numbering) is occupied by L, position L36 (Kabat numbering) is occupied by Y, position L46 (Kabat numbering) is occupied by L, position H1 (Kabat numbering) is occupied by E, position H3 (Kabat numbering) is occupied by K, position H5 (Kabat numbering) is occupied by V, position H42 (Kabat numbering) is occupied by E, and position H83 (Kabat numbering) is occupied by R. In some antibodies, position L3 (Kabat numbering) is occupied by V, position L36 (Kabat numbering) is occupied by F, position L46 (Kabat numbering) is occupied by R, position H1 (Kabat numbering) is occupied by Q, position H3 (Kabat numbering) is occupied by Q, position H5 (Kabat numbering) is occupied by Q, position H42 (Kabat numbering) is occupied by D, and position H83 (Kabat numbering) is occupied by K. In some antibodies, position L3 (Kabat numbering) is occupied by L, position L36 (Kabat numbering) is occupied by Y, position L46 (Kabat numbering) is occupied by L, position H1 (Kabat numbering) is occupied by Q, position H3 (Kabat numbering) is occupied by Q, position H5 (Kabat numbering) is occupied by Q, position H42 (Kabat numbering) is occupied by D, and position H83 (Kabat numbering) is occupied by K. In some antibodies, position L3 (Kabat numbering) is occupied by V, position L36 (Kabat numbering) is occupied by F, position L46 (Kabat numbering) is occupied by R, position H1 (Kabat numbering) is occupied by E, position H3 (Kabat numbering) is occupied by K, position H5 (Kabat numbering) is occupied by V, position H42 (Kabat numbering) is occupied by E, and position H83 (Kabat numbering) is occupied by R.

The invention further provides an antibody comprising the mature heavy chain variable region having an amino acid sequence of SEQ ID NO:11 or SEQ ID NO:17 and a mature light chain variable region having an amino acid sequence of SEQ ID NO:14 or SEQ ID NO:18. In some antibodies, the mature heavy chain variable region has an amino acid sequence of SEQ ID NO:11 and the mature light chain variable region has an amino acid sequence of SEQ ID NO:14. In some antibodies, the mature heavy chain variable region has an amino acid sequence of SEQ ID NO:17 and the mature light chain variable region has an amino acid sequence of SEQ ID NO:18. In some antibodies, the mature heavy chain variable region has an amino acid sequence of SEQ ID NO:11 and the mature light chain variable region has an amino acid sequence of SEQ ID NO:18. In some antibodies, the mature heavy chain variable region has an amino acid sequence of SEQ ID NO:17 and the mature light chain variable region has an amino acid sequence of SEQ ID NO:14.

In any of the above antibodies, the mature heavy chain variable region can be fused to a heavy chain constant region and the mature light chain constant region can be fused to a light chain constant region.

In any of the above antibodies, the heavy chain constant region can be a mutant form of natural human constant region which has reduced binding to an Fcγ receptor relative to the natural human constant region.

In any of the above antibodies, the heavy chain constant region can be of human IgG1 isotype. In some antibodies the allotype is G1m3. In some antibodies, the allotype is G1m1.

In some antibodies, the heavy chain constant region has the amino acid sequence designated SEQ ID NO:37, 38, 39, or 40 provided the C-terminal lysine residue may be omitted. In some antibodies, the light chain constant region has the amino acid sequence designated SEQ ID NO:35. In some antibodies, the mature heavy chain variable region is fused to a heavy chain constant region having the amino acid sequence designated SEQ ID NO:39 provided the C-terminal lysine residue may be omitted and the mature light chain constant region is fused to a light chain constant region having the amino acid sequence designated SEQ ID NO:35. In some antibodies, the mature light chain comprises SEQ ID NO:16 and the mature heavy chain comprises SEQ ID NO:13. In some antibodies, the mature heavy chain variable region has the amino acid sequence of SEQ ID NO:11, the heavy chain constant region has the amino acid sequence of SEQ ID NO:39, the mature light chain variable region has the amino acid sequence of SEQ ID NO:14 and the light chain constant region has the amino acid sequence of SEQ ID NO:35.

The invention further provides a nucleic acid encoding any of the above-mentioned mature heavy chain variable regions and/or any of the above-mentioned mature light chain variable region, e.g., SEQ ID NO:12 or SEQ ID NO:15.

The invention further provides a host cell comprising a vector comprising any of the nucleic acids described above.

The invention further provides a pharmaceutical composition comprising any of the above-mentioned antibodies.

The invention further provides a method of humanizing an antibody, comprising determining the sequences of the heavy and light chain variable regions of a mouse antibody, synthesizing a nucleic acid encoding a humanized heavy chain comprising CDRs of the mouse heavy chain and a nucleic acid encoding a humanized light chain comprising CDRs of the mouse light chain and expressing the nucleic acids in a host cell to produce a humanized antibody, wherein the mouse antibody is 12C12, 15E10 or 15G8.

The invention further provides a method of producing a humanized, chimeric or veneered antibody, comprising culturing cells transformed with nucleic acids encoding the heavy and light chains of the antibody, so that the cells secrete the antibody; and purifying the antibody from cell culture media; wherein the antibody is a humanized, chimeric or veneered form of 12C12, 15E10 or 15G8.

The invention further provides a method of producing a cell line producing a humanized, chimeric or veneered antibody, comprising introducing a vector encoding heavy and light chains of an antibody and a selectable marker into cells, propagating the cells under conditions to select for cells having increased copy number of the vector, isolating single cells from the selected cell, and banking cells cloned from a single cell selected based on yield of antibody; wherein the antibody is a humanized, chimeric or veneered form of 12C12, 15E10 or 15G8. Optionally, the method further comprises propagating the cells under selective conditions and screening for cell lines naturally expressing and secreting at least 100 pg/L/day.

The invention further provides an isolated antibody that specifically binds to ApoE(1-299) at an epitope including residues 272 and 273.

The invention further provides a pharmaceutical composition comprising any of the above antibodies and a pharmaceutically acceptable carrier.

The invention further provides an isolated fragment of ApoE including 3-10 contiguous residues of ApoE and having a C-terminus ending at residue 272. Optionally, the isolated fragment is linked to a carrier molecule optionally via a spacer that helps elicit antibodies against the fragment. The fragment can be combined with an adjuvant acceptable for administration to humans to form a pharmaceutical composition.

The invention further provides a method of treating or effecting prophylaxis of Alzheimer's disease comprising administering an effective regime of an antibody that preferentially binds to ApoE(1-272) relative to ApoE(1-299), or an agent that induces such an antibody, to a patient having or at risk of Alzheimer's disease and thereby treating or effecting prophylaxis of the disease. Any of the antibodies described above can be used in such methods.

In some methods, the antibody comprises a mature heavy chain variable region comprising the three Kabat CDRs of SEQ ID NO:9, and having at least 90% sequence identity to SEQ ID NO:9, and a mature light chain variable region comprising the three Kabat CDRs of SEQ ID NO:10, and having at least 90% sequence identity to SEQ ID NO:10. In some methods, the antibody is a humanized 15G8 antibody comprising a mature light chain variable region framework having at least 85% sequence identity to AAT86035 (SEQ ID NO:8). In some methods, the antibody is a humanized 15G8 antibody comprising a mature heavy chain variable region framework having at least 85% sequence identity to AAX82494 (SEQ ID NO:7). In some methods, the antibody comprises a mature heavy chain variable region having at least 90% sequence identity to SEQ ID NO:17, and a mature light chain variable region having at least 90% sequence identity to SEQ ID NO:18. In some methods, the antibody comprises a mature heavy chain variable region having an amino acid sequence of SEQ ID NO:17 and a mature light chain variable region having an amino acid sequence of SEQ ID NO:18 provided that position L3 (Kabat numbering) can be occupied by V or L, position L36 (Kabat numbering) can be occupied by F or Y, position L46 (Kabat numbering) can be occupied by R or L, position H1 (Kabat numbering) can be occupied by Q or E, position H3 (Kabat numbering) can be occupied by Q or K, position H5 (Kabat numbering) can be occupied by Q or V, position H42 (Kabat numbering) can be occupied by D or E, and position H83 (Kabat numbering) can be occupied by K or R. In some methods, the antibody comprises a mature heavy chain variable region having an amino acid sequence of SEQ ID NO:17 and a mature light chain variable region having an amino acid sequence of SEQ ID NO:18 provided that position L3 (Kabat numbering) is occupied by L, position L36 (Kabat numbering) is occupied by Y, and position L46 (Kabat numbering) is occupied by L. In some methods, the antibody comprises a mature heavy chain variable region having an amino acid sequence of SEQ ID NO:17 and a mature light chain variable region having an amino acid sequence of SEQ ID NO:18 provided that position H1 (Kabat numbering) is occupied by E, position H3 (Kabat numbering) is occupied by K, position H5 (Kabat numbering) is occupied by V, position H42 (Kabat numbering) is occupied by E, and position H83 (Kabat numbering) is occupied by R. In some methods, the antibody comprises a mature heavy chain variable region having an amino acid sequence of SEQ ID NO:11 and a mature light chain variable region having an amino acid sequence of SEQ ID NO:14. In some methods, the antibody comprises a mature heavy chain variable region having the amino acid sequence of SEQ ID NO:11, a heavy chain constant region having the amino acid sequence of SEQ ID NO:39, a mature light chain variable region having the amino acid sequence of SEQ ID NO:14 and a light chain constant region having the amino acid sequence of SEQ ID NO:35. Alternatively, a fragment of 3-10 contiguous amino acids of ApoE with a C-terminus at residue 272 can be used. Optionally, such methods are performed on a patient who is an ApoE4 carrier.

The invention further provides a method of treating or effecting prophylaxis of a disease associated with ApoE4 comprising administering an effective regime of an antibody that preferentially binds to ApoE(1-272) relative to ApoE(1-299), or an agent that induces such an antibody, to a patient having or at risk of the disease and thereby treating or effecting prophylaxis of the disease.

The invention further provides a method of treating or effecting prophylaxis of neurological disease comprising administering an effective regime of an antibody that preferentially binds to ApoE(1-272) relative to ApoE(1-299) or an agent that induces such an antibody to a patient who is an ApoE4 carrier and thereby treating or effecting prophylaxis of the disease.

The invention further provides a method of screening an agent for activity against Alzheimer's disease, comprising administering the agent to a transgenic animal expressing ApoE and amyloid beta precursor (APP) transgenes, and determining whether the agent inhibits or delays at least one sign or symptom of Alzheimer's disease, wherein the agent is an antibody that preferentially binds to ApoE(1-272) relative to Apo E(1-299) or the agent induces such an antibody.

BRIEF DESCRIPTION OF THE DRAWINGS

FIG. 1 shows an alignment of the amino acid sequences of mouse 15G8 with the humanized 15G8 heavy chain mature variable region. The human acceptor VH sequence from AAX82494 (GI: 62421461) (SEQ ID NO:7) is used as human acceptor VH sequence.

FIG. 2 shows an alignment of the amino acid sequences of mouse 15G8 with the humanized 15G8 light chain mature variable region. The human acceptor VL sequence from AAT86035 (SEQ ID NO:8) is used as human acceptor VL sequence.

FIG. 4 shows western blot of tissue lysates from wild-type mouse ("wt"), apoE knockout mouse ("KO"), and transgenic mice that express human ApoE knock-in (E2, E3, and E4 strains) and human amyloid beta using monoclonal antibodies 12C12 (left panel), 15E10 (middle panel), and 15G8 (right panel).

BRIEF DESCRIPTION OF THE SEQUENCES

Figure 3:
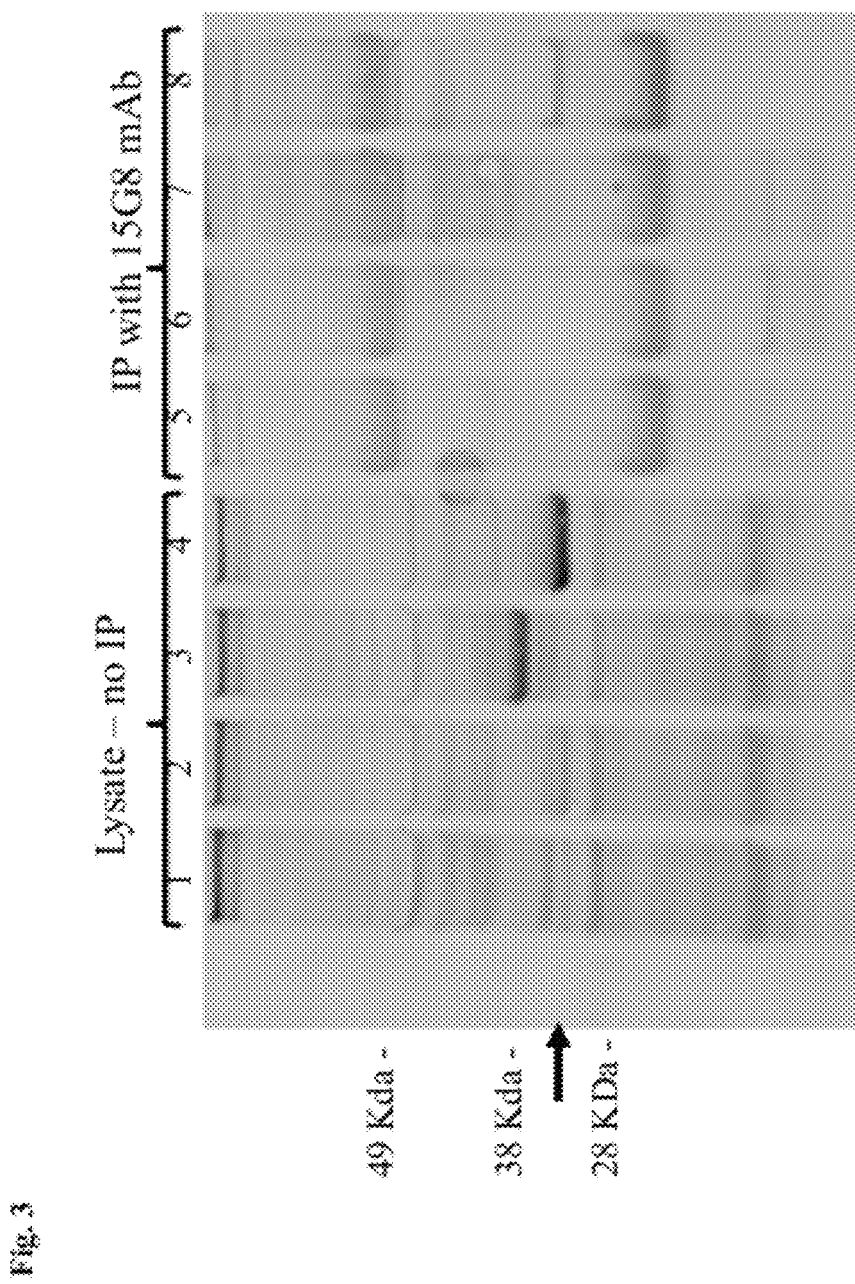
FIG. 3 shows immunoprecipitation blots of full-length ApoE3, full-length ApoE4, ApoE3(1-272), and ApoE4(1-272).

SEQ ID NO:1 is the ApoE3 amino acid sequence.
SEQ ID NO:2 is the ApoE4 amino acid sequence.
SEQ ID NO:3 is the ApoE3 (1-272) amino acid sequence.
SEQ ID NO:4 is the ApoE4 (1-272) amino acid sequence.
SEQ ID NO:5 is ApoE 268-272 with an artificial CGG added as linker and for ease of coupling.
SEQ ID NO:6 is the amino acid sequence of ApoE4 (266-276).
SEQ ID NO:7 is the human acceptor $V_H$ sequence from AAX82494.
SEQ ID NO:8 is the human acceptor $V_L$ sequence from AAT86035.
SEQ ID NO:9 is the amino acid sequence of m15G8VH variable region (same as m12C12VH or m15E10VH).
SEQ ID NO:10 is m15G8VL variable region (same as m12C12VL or m15E10VL).
SEQ ID NO:11 is the amino acid sequence of Hu15G8VHv1 variable region.
SEQ ID NO:12 is the nucleic acid sequence of Hu15G8VHv1 variable region.
SEQ ID NO:13 is the amino acid sequence of Hu15G8VHv1 fused with IgG1 human G1 m3 allotype constant region.
SEQ ID NO:14 is the amino acid sequence of Hu15G8VLv1 variable region.
SEQ ID NO:15 is the nucleic acid sequence of Hu15G8VLv1 variable region.
SEQ ID NO:16 is the amino acid sequence of Hu15G8VLv1 fused with human light chain kappa constant region (with Arginine at the N-terminal of the constant region).
SEQ ID NO:17 is the amino acid sequence of Hu15G8VHv2 variable region having no backmutation in the variable framework region.
SEQ ID NO:18 is the amino acid sequence of Hu15G8VLv2 variable region having no backmutation in the variable framework region.
SEQ ID NO:19 is the amino acid sequence of heavy chain Kabat CDR1.
SEQ ID NO:20 is the amino acid sequence of heavy chain Kabat CDR2.
SEQ ID NO:21 is the amino acid sequence of heavy chain Kabat CDR3.
SEQ ID NO:22 is the amino acid sequence of light chain Kabat CDR1.
SEQ ID NO:23 is the amino acid sequence of light chain Kabat CDR2.
SEQ ID NO:24 is the amino acid sequence of light chain Kabat CDR3.
SEQ ID NO:25 is the amino acid sequence of m15G8VH signal peptide.
SEQ ID NO:26 is the amino acid sequence of m12C12VH signal peptide.
SEQ ID NO:27 is the amino acid sequence of m15E10VH signal peptide.
SEQ ID NO:28 is the amino acid sequence of m15G8VL signal peptide (same as m12C12VL or m15E10VL signal peptides).
SEQ ID NO:29 the nucleic acid sequence of Hu15G8VH signal peptide v1.
SEQ ID NO:30 the amino acid sequence of Hu15G8VH signal peptide v1.
SEQ ID NO:31 the nucleic acid sequence of Hu15G8VH signal peptide v2.
SEQ ID NO:32 the amino acid sequence of Hu15G8VH signal peptide v2.
SEQ ID NO:33 the nucleic acid sequence of Hu15G8VL signal peptide.
SEQ ID NO:34 the amino acid sequence of Hu15G8VL signal peptide.
SEQ ID NO:35 the amino acid sequence of human light chain kappa constant region with arginine at the N-terminal.

SEQ ID NO:36 the amino acid sequence of human light chain kappa constant region without arginine at the N-terminal.

SEQ ID NO:37 the amino acid sequence of human IgG1 heavy chain constant region.

SEQ ID NO:38 the amino acid sequence of human IgG1 G1m1 allotype heavy chain constant region.

SEQ ID NO:39 the amino acid sequence of human IgG1 G1m3 allotype heavy chain constant region.

SEQ ID NO:40 is the amino acid sequence of human IgG2 heavy chain constant region.

SEQ ID NO:41 is ApoE 268-272.

DEFINITIONS

Monoclonal antibodies and other therapeutic agents are typically provided in isolated form. This means that the agent is typically at least 50% w/w pure of interfering proteins and other contaminants arising from its production or purification but does not exclude the possibility that the agent is combined with an excess of pharmaceutical acceptable carrier(s) or other vehicle intended to facilitate its use. Sometimes monoclonal antibodies are at least 60%, 70%, 80%, 90%, 95% or 99% w/w pure of interfering proteins and contaminants from production or purification.

Antibodies of the invention typically bind to their designated target with an association constant of at least $10^6$, $10^7$, $10^8$, $10^9$, or $10^{10}$ $M^{-1}$. Such binding is specific binding in that it is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition, e.g., a variable light chain region (VL) and a variable heavy chain region (VH). This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions (CDRs). The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., Nature 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, fragments compete with the intact antibody from which they were derived for specific binding to the target. Fragments include separate heavy chains, light chains Fab, Fab', F(ab)$_2$, F(ab)c, Fv and single domain antibodies. Single (variable) domain antibodies include VH regions separated from their VL partners (or vice versa) in conventional antibodies (Ward et al., 1989, Nature 341: 544-546) as well as VH regions (sometimes known as VHH) from species such as Camelidae or cartilaginous fish (e.g., a nurse shark) in which VH regions are not associated with VL regions (see, e.g., WO 9404678). The former type of antibodies are sometimes known as Dabs and the latter are sometimes known as nanobodies. Constant regions or parts of constant regions may or may not be present in single domain antibodies. For example, natural single variable domain antibodies from Camelidae include a VHH variable region, and CH2 and CH3 constant regions. Single domain antibodies can be subject of humanization by analogous approaches to conventional antibodies. The Dabs type of antibodies are usually obtained from antibodies of human origin. Nanobody™ types of antibody are of Camelidae or shark origin and can be subject to humanization. Fragments can be produced by recombinant DNA techniques, or by enzymatic or chemical separation of intact immunoglobulins. As well as monospecific antibodies, the term "antibody" also includes a bispecific antibody. A bispecific or bifunctional antibody is an artificial hybrid antibody having two different heavy/light chain pairs and two different binding sites (see, e.g., Songsivilai and Lachmann, Clin. Exp. Immunol. 79:315-321 (1990); Kostelny et al., J. Immunol., 148:1547-53 (1992)). In some bispecific antibodies, the two different heavy/light chain pairs include a monoclonal or humanized 15G8 heavy chain/light chain pair and a heavy chain/light chain pair specific for a different epitope on ApoE than that bound by 15G8.

In some bispecific antibodies, one heavy chain/light chain pair is a monoclonal or humanized 15G8 antibody as further disclosed below and the heavy/light chain pair is from an antibody that binds to a receptor expressed on the blood brain barrier, such as an insulin receptor, an insulin-like growth factor (IGF) receptor, a leptin receptor, a lipoprotein receptor, or a transferrin receptor (Friden et al., PNAS 88:4771-4775, 1991; Friden et al., Science 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor has resulted in a broader distribution in the brain (see, e.g., Atwal. et al. *Sci. Trans. Med.* 3, 84ra43, 2011; Yu et al. *Sci. Trans. Med.* 3, 84ra44, 2011).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): tip, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "adjuvant" refers to a compound that when administered in conjunction with an antigen augments and/or redirects the immune response to the antigen, but when administered alone does not generate an immune response to the antigen. Adjuvants can augment an immune response by several mechanisms including lymphocyte recruitment, stimulation of B and/or T cells, and stimulation of macrophages.

For brevity, the term "ApoE4 carrier" is sometimes used to refer to patients having one or two ApoE4 alleles and "ApoE4 noncarrier", "ApoE4 non-carrier" or "non-ApoE4 carrier" to refer to patients having zero ApoE4 alleles.

A disease is associated with the ApoE4 allele if a population of ApoE4 carriers has a greater frequency of occurrence of the disease, greater severity of the disease or earlier age of onset of the disease compared with a population of non-carriers to a statistically significant extent.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor.

The term "symptom" refers to subjective evidence of a disease, such as altered gait, as perceived by the patient. A "sign" refers to objective evidence of a disease as observed by a physician.

Statistical significance means $p \leq 0.05$.

DETAILED DESCRIPTION OF THE INVENTION

I. General

Normal human ApoE is 299 amino acids in length not including a signal peptide but can be truncated by cleavage with a chymotrypsin-like serine protease in vivo to generate C-terminal truncations and particularly a fragment truncated at amino acid 272. ApoE4 more readily undergoes proteolytic cleavage than other ApoE isoforms. The 1-272 fragment of ApoE4 is neurotoxic in tissue culture and in transgenic mice expressing the 1-272 fragment.

The present invention provides antibodies that preferentially bind to an ApoE(1-272) fragment relative to ApoE(1-299) or relative to other C-terminally truncated form of ApoE terminating at residue 273 or greater. These antibodies serve to reduce the toxicity of this fragment. Although an understanding of mechanism is not required for practice of the invention, a reduction in toxicity may occur as a result of the antibody inducing phagocytosis of the fragment, or reducing the free concentration of ApoE(1-272), or inhibiting the fragment from inter or intramolecular aggregation, or from binding to other molecules, or by stabilizing a non-toxic conformation among other mechanisms. Because the antibody preferentially binds to ApoE(1-272) over full-length ApoE, the toxicity of truncated fragments can be inhibited without unacceptable reduction of the neuroprotective role of full length ApoE(1-299).

Antibodies that preferentially bind to an ApoE(1-272) fragment or agents that can induce such antibodies can be used in methods of treating or effecting prophylaxis of Alzheimer's disease and other diseases associated with the presence of ApoE4.

II. ApoE and Fragments Thereof

Unless otherwise apparent from the context, ApoE refers to a natural human form of ApoE, particularly the ApoE2, E3 or E4 allele thereof. An exemplary sequence of the E3 allele (residues 19-317 of Swiss-Prot P02649) is provided below.

```
                                                             (SEQ ID NO: 1)
KVEQAVETEP EPELRQQTEW QSGQRWELAL GRFWDYLRWV QTLSEQVQEE LLSSQVTQEL RALMDETMKE

LKAYKSELEE QLTPVAEETR ARLSKELQAA QARLGADMED VCGRLVQYRG EVQAMLGQST EELRVRLASH

LRKLRKRLLR DADDLQKRLA VYQAGAREGA ERGLSAIRER LGPLVEQGRV RAATVGSLAG QPLQERAQAW

GERLRARMEE MGSRTRDRLD EVKEQVAEVR AKLEEQAQQI RLQAEAFQAR LKSWFEPLVE DMQRQWAGLV

EKVQAAVGTS AAPVPSDNH
```

The underlined cysteine at position 112 is arginine in ApoE4 and the underlined arginine at position 158 is cysteine in ApoE2. Thus, ApoE4 has the following sequence

```
                                                             (SEQ ID NO: 2)
KVEQAVETEP EPELRQQTEW QSGQRWELAL GRFWDYLRWV QTLSEQVQEE LLSSQVTQEL RALMDETMKE

LKAYKSELEE QLTPVAEETR ARLSKELQAA QARLGADMED VRGRLVQYRG EVQAMLGQST EELRVRLASH

LRKLRKRLLR DADDLQKRLA VYQAGAREGA ERGLSAIRER LGPLVEQGRV RAATVGSLAG QPLQERAQAW

GERLRARMEE MGSRTRDRLD EVKEQVAEVR AKLEEQAQQI RLQAEAFQAR LKSWFEPLVE DMQRQWAGLV

EKVQAAVGTS AAPVPSDNH
```

Fragments of ApoE are sometimes referred to by providing a range of the first and last amino acid, as for example ApoE (1-272). As for the full length ApoE protein, such a fragment can include any of the E2, E3 or E4 alleles. A preferred fragment is ApoE(1-272). The E3 and E4 alleles of this fragment are shown below, with E3 first.

```
                                                             (SEQ ID NO: 3)
KVEQAVETEP EPELRQQTEW QSGQRWELAL GRFWDYLRWV QTLSEQVQEE LLSSQVTQEL RALMDETMKE

LKAYKSELEE QLTPVAEETR ARLSKELQAA QARLGADMED VCGRLVQYRG EVQAMLGQST EELRVRLASH

LRKLRKRLLR DADDLQKRLA VYQAGAREGA ERGLSAIRER LGPLVEQGRV RAATVGSLAG QPLQERAQAW

GERLRARMEE MGSRTRDRLD EVKEQVAEVR AKLEEQAQQI RLQAEAFQAR LKSWFEPLVE DM
```

```
                                                             (SEQ ID NO: 4)
KVEQAVETEP EPELRQQTEW QSGQRWELAL GRFWDYLRWV QTLSEQVQEE LLSSQVTQEL RALMDETMKE

LKAYKSELEE QLTPVAEETR ARLSKELQAA QARLGADMED VRGRLVQYRG EVQAMLGQST EELRVRLASH

LRKLRKRLLR DADDLQKRLA VYQAGAREGA ERGLSAIRER LGPLVEQGRV RAATVGSLAG QPLQERAQAW

GERLRARMEE MGSRTRDRLD EVKEQVAEVR AKLEEQAQQI RLQAEAFQAR LKSWFEPLVE DM
```

The allelic forms present in any individual can be determined by many conventional techniques, such as direct sequencing, use of GeneChip® arrays or the like, allele-specific probes, single-base extension methods, allelic specific extension. Allelic forms can also be determined at the protein level by ELISA using antibodies specific for different allelic expression products. Kits for genetic and immunological analysis are commercially available (e.g., Innogenetics, Inc.). Determination of allelic forms are usually made in vitro, that is, on samples removed and never returned to a patient.

III. Antibodies

A. Binding Specificity and Functional Properties

The invention provides antibodies preferentially binding to ApoE(1-272) relative to ApoE(1-299). The antibodies can be monoclonal or polyclonal. Antibodies designated 12C12, 15E10 or 15G8 are three exemplary mouse monoclonal antibodies of IgG1k isotype. The mouse monoclonal antibodies 12C12, 15E10, and 15G8 have the same mature variable regions. The mature heavy chain variable region of mouse monoclonal 12C12, 15E10, or 15G8 is SEQ ID NO:9. The mature light chain variable region of mouse monoclonal 12C12, 15E10 or 15G8 is SEQ ID NO:10.

>m15G8VH variable region (same as m12C12VH or m15E10VH)

```
                                                             (SEQ ID NO: 9)
EVKLVESGGGLVKPGGSLKLSCAASGFTFS*FYAMS*WVRQTPEKRLEWVA

*SLSRGGSTYYPDSVKG*RFTISRDNARNTLYLQMSSLRSEDTAMFYCA

R*EGATALYAMDY*WGQGTSVTVSS
```

>m15G8VL variable region (same as m12C12VL or m15E10VL)

(SEQ ID NO: 10)
DVLMTQTPLSLPVSLGDQASISCRSSQSIVHSNGNTYLQWYLQKPGQSPKLLIYKVSNRF

SGVPDRFSGSGSGTDFTLKISRVEAEDLGIYYCFQGSHVPWTFGGGTKLEIK

Preferential binding means that an antibody binds to ApoE (1-272) detectably more strongly (i.e., higher association constant) than to ApoE(1-299) (i.e., beyond experimental error). Preferred antibodies have association constants at least 2, 5 or 10-fold higher for ApoE(1-272) than ApoE(1-299). Some antibodies bind to ApoE(1-272) and lack any significant binding to ApoE(1-299) (i.e., binding indistinguishable between ApoE(1-299) and an irrelevant control protein). Some antibodies preferentially binding to ApoE(1-272) over ApoE(1-299) are end-specific for the free C-terminus of ApoE(1-272). Such antibodies recognize an epitope including the C-terminal amino acid of ApoE(1-272) in free form (i.e., with a carboxyl group not attached to another amino acid as occurs in ApoE(1-299)). End-specific antibodies can bind for example to an epitope within residues 263-272, 264-272, 265-272, 266-272, 267-272, 268-272, 269-272 or 270-272 of ApoE (within being inclusive of the positions used to define the range). End-specific antibodies to ApoE(1-272) show preferential binding for ApoE(1-272) relative to ApoE(1-299) but may or may not lack any degree of specific binding to ApoE(1-299). Other antibodies preferentially binding to ApoE(1-272) over ApoE(1-299) are not end-specific but may recognize a conformational epitope present on ApoE(1-272) that is not present or at least not precisely replicated in ApoE (1-299) due for example to differences in folding patterns between ApoE(1-272) and ApoE(1-299).

End-specific antibodies to the C-terminus of ApoE(1-272) can be generated de novo by immunizing with a peptide including the C-terminal amino acid of this fragment. Usually, such peptides have 3-10 contiguous amino acids from the C-terminus including the C-terminal amino acid, with peptides of 5 or 6 contiguous amino acids being preferred. Such peptides are preferably attached to a heterologous conjugate molecule that helps elicit an antibody response to the peptide. Attachment can be direct or via a spacer peptide or amino acid. Cysteine is used as a spacer amino acid because its free SH group facilitates attachment of a carrier molecule. A polyglycine linker (e.g., 2-6 glycines), with or without a cysteine residue between the glycines and the peptide can also be used. The carrier molecule serves to provide a T-cell epitope that helps elicit an antibody response against the peptide. Several carriers can be used, including keyhole limpet hemocyanin (KLH), ovalbumin and bovine serum albumin (BSA). Peptide spacers can be added to the peptide immunogen as part of solid phase peptide synthesis. Peptide spacers can be added to peptide immunogen as part of solid phase peptide synthesis. Carriers are typically added by chemical cross-linking. Some examples of chemical crosslinkers that can be used include cross-N-maleimido-6-aminocaproyl ester or m-maleimidobenzoyl-N-hydroxysuccinimide ester (MBS) (see for example, Harlow, E. et al., Antibodies: A Laboratory Manual, Cold Spring Harbor Laboratory Press, Cold Spring Harbor, N.Y. 1988; Sinigaglia et al., Nature, 336:778-780 (1988); Chicz et al., J. Exp. Med., 178: 27-47 (1993); Hammer et al., Cell 74:197-203 (1993); Falk K. et al., Immunogenetics, 39:230-242 (1994); WO 98/23635; and, Southwood et al. J. Immunology, 160:3363-3373 (1998).). Because the goal is to generate antibodies to the free C-terminus of the peptide, the carrier and spacer if present are typically attached to the N-terminus of the peptide. Exemplary protocols for generating end-specific antibodies against other peptides are described by e.g., Konig, Ann N.Y. Acad Sci 777:344-355 (1996), Harrington, Biochim. Biophys. Acta 1158 (2):120-128 (1993); Gravina et al., J. Biol. Chem. 270:(13):7013-6 (1995).

A peptide with optional spacer and carrier can be used to immunize a laboratory animals or B-cells as described in more detail below. Hybridoma supernatants can be tested for ability to bind the ApoE peptide used as an immunogen. The peptide can be attached to a carrier or other tag to facilitate the screening assay. In this case, the carrier or tag is preferentially different than the combination of spacer and carrier molecule used for immunization to eliminate antibodies specific for the spacer or carrier rather than the ApoE peptide. Antibodies can also be screened against a peptide bridging the site of truncation of the peptide immunogen. For example, if the peptide immunogen ends at residue 272 of ApoE, a peptide bridging the site of truncation includes at least residues 272 and 273 of ApoE. Antibodies can also be screened for binding to ApoE (1-272) and for lack of binding or at least reduced binding to ApoE(1-299). The ApoE used in such assays can be any of the E2, E3 or E4 isoforms.

Some antibodies of the invention bind to the same or overlapping epitope as mouse monoclonal antibodies 12C12, 15E10 or 15G8. Some antibodies compete for specific binding to ApoE with a mouse monoclonal antibody 12C12, 15E10 or 15G8. Antibodies having such a binding epitope or specificity can be produced by immunizing mice with ApoE or a portion thereof including the desired epitope, and screening resulting antibodies for preferentially binding to ApoE(1-272) relative to ApoE(1-299), optionally in competition with a mouse monoclonal antibody 12C12, 15E10 or 15G8.

Antibodies having the binding specificity of a selected murine antibody (e.g. 12C12, 15E10 or 15G8) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for ApoE (1-272) (e.g., at least $10^8$ and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for Apo E(1-272) are selected. The resulting antibodies usually have the same or similar epitope specificity as the murine starting material.

Other antibodies can be obtained by mutagenesis of cDNA encoding the heavy and light chains of an exemplary antibody, such as 12C12, 15E10 or 15G8. Monoclonal antibodies that are at least 62.5%, 65%, 75%, 85%, 90%, 95% or 99% identical to 12C12, 15E10 or 15G8 in amino sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. In some such antibodies, each CDR differs in sequence from a corresponding CDR from 15G8 by no more than 6 (e.g., 1, 2, 3, 4, 5, or 6) replacements, deletions or insertions. Monoclonal antibodies having at least one and preferably all six CDR(s) as defined by Kabat that are at least 62.5%, 65%, 75%, 85%, 90%, 95%, 99% or 100% identical to corresponding CDRs of 12C12, 15E10 or 15G8 are also included. Some antibodies have at least 80, 95 or 100% identity to each CDR of 12C12, 15E10 or 15G8 other than CDR H2 and at least 62.5% identity to CDR H2. The mouse monoclonal antibodies 12C12, 15E10, and 15G8 each have three Kabat light chain CDRs of SEQ ID NO:22, SEQ ID NO:23, and SEQ ID NO:24, and three Kabat heavy chain CDRs of SEQ ID NO:19, SEQ ID NO:20, and SEQ ID NO:21.

```
heavy chain Kabat CDR1
                               (SEQ ID NO: 19)
FYAMS heavy chain Kabat CDR2
                               (SEQ ID NO: 20)
SLSRGGSTYYPDSVKG heavy chain Kabat CDR3
                               (SEQ ID NO: 21)
EGATALYAMDY light chain Kabat CDR1
                               (SEQ ID NO: 22)
RSSQSIVHSNGNTYLQ light chain Kabat CDR2
                               (SEQ ID NO: 23)
KVSNRFS light chain CDR3 Kabat
                               (SEQ ID NO: 24)
FQGSHVPWT
```

Antibodies discriminating between ApoE(1-272) and ApoE(1-299) that are not end-specific but bind to conformational epitopes present in ApoE(1-272) but not present or not precisely replicated in ApoE(1-299) can be produced by immunizing with longer peptide immunogens sufficient to develop a characteristic conformation, for example ApoE(1-272) itself or at least 50, 100, 200 or 250 contiguous residues thereof. Longer peptides can be produced by recombinant expression among other methods. Antibodies generated by such methods are screened for preferential binding to ApoE (1-272) relative to ApoE(1-299).

The invention also provides antibodies that preferably bind to longer truncated fragments, i.e., fragments from ApoE(1-273) to ApoE(1-298) relative to ApoE(1-299) including antibodies that are end-specific for the C-terminus of such fragments.

The invention also provides antibodies having an epitope including the two residues on either side of a site of proteolytic cleavage. For the site of cleavage, generating ApoE (1-272), the two such residues are residues 272 and 273 of ApoE. Such antibodies can be generated using a peptide as immunogen including the two residues on either side of the cleavage site. As in generating an end-specific antibody, such a peptide typically includes about 3-10 contiguous amino acids from ApoE altogether. The peptide can be linked to a conjugate molecule optionally via a spacer as described in producing end-specific antibodies.

B. Non-Human Antibodies

The production of other non-human monoclonal antibodies, e.g., murine, guinea pig, primate, rabbit or rat, against an immunogen can be performed by, for example, immunizing the animal with an immunogen as described above. See Harlow & Lane, *Antibodies, A Laboratory Manual* (CSHP N.Y., 1988) (incorporated by reference for all purposes). Such an immunogen can be obtained from a natural source, by peptide synthesis or by recombinant expression.

Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to ApoE(1-272) or other truncated form of ApoE. Optionally, antibodies are further screened for lack of specific binding to ApoE(1-299) or to a peptide of ApoE including residues spanning residues 272-273 or a peptide spanning another cleavage site generating a truncated form of ApoE. Such screening can be accomplished by determining binding of an antibody to a collection of deletion mutants and determining which deletion mutants bind to the antibody. Binding can be assessed, for example, by Western blot, FACS™ or ELISA.

C. Humanized Antibodies

A humanized antibody is a genetically engineered antibody in which the CDRs from a non-human "donor" antibody (e.g., 12C12, 15E10 or 15G8) are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. Nos. 5,859, 205 and 6,881,557, and Foote, U.S. Pat. No. 6,881,557). The acceptor antibody sequences can be, for example, a mature human antibody sequence, a composite of such sequences, a consensus sequence of human antibody sequences (e.g., light or heavy chain variable region consensus sequences of Kabat, 1991, supra), or a germline variable region sequence.

An example of an acceptor sequence for the heavy chain is the human mature heavy chain variable region with GenBank accession code AAX82494 (GI: 62421461). CDR H1 and H2 of this acceptor sequence are of the same canonical forms as those of mouse 15G8 heavy chain (CDR H3 of 15G8 has no canonical class). This acceptor sequence has a sequence identity of 82% in the heavy chain variable region framework to mouse 15G8 heavy chain variable region framework. If a different acceptor sequence is used, such an acceptor can be, for example, a mature heavy chain variable region derived from the human mature heavy chain variable region with GenBank accession code AAL57837 (GI: 18042117; 77% sequence identity to mouse 15G8 heavy chain variable region framework) or a mature heavy chain variable region sequence incorporating one of such sequences.

For the light chain, an example of an acceptor sequence is the mature light chain variable region with GenBank accession code AAT86035 (GI:50898163). This acceptor sequence includes three CDRs having the same canonical form as a mouse 15G8 light chain and has a sequence identity of 81% in the light chain variable region framework. If a different acceptor is used, such an acceptor can be, for example, another mature light chain sequence derived from the mature light chain variable region with GenBank accession code BAC01730 (GI:21669411; 81% sequence identity to mouse 15G8 light chain variable region framework) or ABC66863

(GI: 84797828; 80% sequence identity to mouse 15G8 light chain variable region framework) or a mature light chain variable region sequence incorporating one of such sequences.

A humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41: 863, 2004. Thus, for example, some humanized antibodies can have a CDR H2 with up to 6 replacements, deletions or insertions, or at least 62.5% sequence identity with CDR H2 of the donor antibody. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:
   (1) noncovalently binds antigen directly,
   (2) is adjacent to a CDR region,
   (3) otherwise interacts with a CDR region (e.g. is within about 6 Å of a CDR region), (e.g., identified by modeling the light or heavy chain on the solved structure of a homologous known immunoglobulin chain); and
   (4) a residue participating in the VL-VH interface.

Framework residues from classes (1)-(3) as defined by Queen, U.S. Pat. No. 5,530,101 are sometimes alternately referred to as canonical and vernier residues. Framework residues defining canonical class of the donor CDR loops determining the conformation of a CDR loop are sometimes referred to as canonical residues (Chothia and Lesk, J. Mol. Biol. 196, 901-917 (1987), Thornton & Martin *J. Mol. Biol.,* 263, 800-815, 1996). A layer of framework residues that support antigen-binding loop conformations play a role in fine-tuning the fit of an antibody to antigen are sometimes referred to as vernier residues (Foote & Winter, 1992, *J Mol Bio.* 224, 487-499). Other candidates for substitution are residues creating a potential glycosylation site. Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position.

Exemplary humanized antibodies of the invention include a humanized form of 15G8, characterized by a mature light chain variable region of SEQ ID NO:14 or SEQ ID NO:18 (designated L1 and L2, respectively) and a mature heavy chain variable region of SEQ ID NO:11 or SEQ ID NO:17 (designated H1 and H2, respectively). For example, humanized antibodies include H1L1, H2L2, H1L2, and H2L1.

The invention also provides variants of H1L1, H2L2, H1L2, and H2L1. In such variants, the humanized heavy chain mature variable region shows at least 65%, 85%, 90%, 93%, 94%, 95%, 96%, 97%, 98% or 99% identity to SEQ ID NO:11 or SEQ ID NO:17 and the humanized light chain mature variable region shows at least 65%, 85%, 90%, 93%, 94%, 95%, 96%, 97%, 98% or 99% sequence identity to SEQ ID NO:14 or SEQ ID NO:18. Some such humanized antibodies include three heavy and three light chain Kabat CDRs entirely or substantially identical to the Kabat CDR regions of H1L1, H2L2, H1L2, and H2L1, which are the same as those of the mouse donor antibody.

Some variants differ from the sequences of H1L1, H2L2, H1L2, or H2L1 by a small number (e.g., typically no more than 1, 2, 3, 5, 6, 7, 8, 9 or 10) of replacements, deletions or insertions. Such differences are usually in the framework but can also occur in the CDRs. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution or even amino acids within the CDRs may be altered. One example of a CDR substitution is to substitute a residue in a CDR with the residue occupying the corresponding position of the human acceptor sequence used to supply variable region frameworks.

Often the replacements made in the variants of H1L1, H2L2, H1L2, and H2L1 are conservative with respect to the replaced amino acids. In some variants, replacements in H1L1, H2L2, H1L2, and H2L1 (whether or not conservative) have no substantial effect on the binding affinity of the humanized antibody. In some variants, the mature variant light and heavy chain variable region sequences are at least 90%, at least 93%, at least 94%, at least 95%, at least 96%, at least 97%, or at least 98% identical to the respective H1L1, H2L2, H1L2, and H2L1 mature light and heavy chain variable regions. Alternatively, other human antibody acceptor sequences, particularly those with high sequence identity to the variable region framework sequences of murine 15G8 are also suitable to provide the humanized antibody variable regions framework sequences.

In some variants of H1L1, H2L2, H1L2, and H2L1, at least 1, 2, 3, 4, 5, 6, 7 or all 8 of the positions of acceptor to donor substitutions mentioned in connection with the exemplified antibody (i.e., L3, L36, L46, H1, H3, H5, H42, and H83) are occupied by residues L, Y, L, E, K, V, E, and R respectively (the residues occupying the corresponding position of the mouse donor antibody heavy chain). If the heavy chain acceptor sequence is other than AAX82494, or the light chain acceptor sequence is other than AAT86035 an acceptor to donor substitution may or may not be required for the specified occupancy of a particular variable framework region position depending on whether the residue occupying the specified position is already the same between the acceptor and donor.

D. Chimeric and Veneered Antibodies

The invention further provides chimeric and veneered forms of non-human antibodies, particularly the 12C12, 15E10 or 15G8 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

E. Human Antibodies.

Human antibodies against ApoE(1-272) or other truncated form of ApoE are provided by a variety of techniques described below. Methods for producing human antibodies include the trioma method of Oestberg et al., Hybridoma 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, Nature 148, 1547-1553 (1994), Nature Biotechnology 14, 826 (1996), Kucherlapati, WO 91/10741 (1991) and phage display methods (see, e.g. Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332.

F. Selection of Constant Region

The heavy and light chain variable regions of chimeric, humanized (including veneered), or human antibodies can be linked to at least a portion of a human constant region. The choice of constant region depends, in part, whether antibody-dependent complement and/or cellular mediated cytotoxicity is desired. For example, human isotypes IgG1 and IgG3 have complement-mediated cytotoxicity and human isotypes IgG2 and IgG4 do not. Light chain constant regions can be lambda or kappa.

An exemplary human light chain kappa constant region has the amino acid sequence of SEQ ID NO:35. The N-terminal arginine of SEQ ID NO:35 can be omitted, in which case light chain kappa constant region has the amino acid sequence of SEQ ID NO:36. An exemplary human IgG1 heavy chain constant region has the amino acid sequence of SEQ ID NO:37. An exemplary human IgG2 heavy chain constant region has the amino acid sequence of SEQ ID NO:38. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes. Reference to a human constant region includes a constant region with any natural allotype or any permutation of residues occupying polymorphic positions in natural allotypes or up to 3, 5 or 10 substitutions for reducing or increasing effector function as described below. For example, heavy chain constant regions can be of IgG1 G1m1 or IgG1 G1m3 allotypes and have the amino acid sequence of SEQ ID NO:38 or SEQ ID NO:39, respectively. Yet another heavy chain constant region has the amino acid sequence of SEQ ID NO:38 or SEQ ID NO:39 except that it lacks the C-terminal lysine.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half life of an antibody. Substitution at any or all of positions 234, 235, 236 and/or 237 reduce affinity for Fcγ receptors, particularly FcγRI receptor (see, e.g., U.S. Pat. No. 6,624,821). An alanine substitution at positions 234, 235 and 237 of human IgG1 is preferred for reducing effector functions. Optionally, positions 234, 236 and/or 237 in human IgG2 are substituted with alanine and position 235 with glutamine (See, e.g., U.S. Pat. No. 5,624,821).

In some antibodies, the light chain constant region has the amino acid sequence of SEQ ID NO:35. In some antibodies, the heavy chain constant region has the amino acid sequence of SEQ ID NO:39. An exemplary humanized light chain has an amino acid sequence of SEQ ID NO:16. An exemplary humanized heavy chain has the amino acid sequence of SEQ ID NO:13.

>Hu15G8VHv1 fused with IgG1 human G1 m3 allotype constant region

```
                                                    (SEQ ID NO: 13)
EVKLVESGGGLVKPGGSLKLSCAASGFTFSFYAMSWVRQTPEKRLEWVASLSRGGSTY

YPDSVKGRFTISRDNAKNTLYLQMSSLRSEDTAMYYCAREGATALYAMDYWGQGTM

VTVSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

ELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYSK

LTVDKSRWQQGNVFSCSVMHEALHNHYTQKSLSLSPGK
```

>Hu15G8VLv1 fused with human light chain kappa constant region (with Arginine at the N-terminal of the constant region)

```
                                                    (SEQ ID NO: 16)
DVLMTQSPLSLPVTLGQPASISCRSSQSIVHSNGNTYLQWYLQRPGQSPRLLLYKVSNRF

SGVPDRFSGSGSGTDFTLKISRVEAEDVGVYYCFQGSHVPWTFGQGTKVEIKRTVAAPS

VFIFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC
```

G. Expression of Recombinant Antibodies

Chimeric, humanized (including veneered) and human antibodies are typically produced by recombinant expression. Nucleic acids encoding the antibodies can be codon-optimized for expression in the desired cell-type (e.g., CHO or Sp2/0). Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. The vector or vectors encoding the antibody chains can also contain a selectable gene, such as dihydrofolate reductase, to allow amplification of copy number of the nucleic acids encoding the antibody chains.

E. coli is a prokaryotic host particularly useful for expressing antibodies, particularly antibody fragments. Microbes, such as yeast are also useful for expression. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilizations Mammalian cells are a preferred host for expressing nucleotide segments encoding immunoglobulins or fragments thereof. See Winnacker, From Genes to Clones, (VCH Publishers, N.Y., 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivites above 50 pg or 100 pg per cell per day, which correspond to product titers of greater than 7.5 g/L culture, are preferred. Antibodies produced by single cell clones can also be tested for turbidity, filtration properties, PAGE, IEF, UV scan, HP-SEC, carboydrate-oligosaccharide mapping, mass spectrometery, and binding assay, such as ELISA or Biacore. A selected clone can then be banked in multiple vials and stored frozen for subsequent use.

Once expressed, antibodies can be purified according to standard procedures of the art, including protein A capture, column chromatography (e.g., hydrophobic interaction or ion exchange), low-pH for viral inactivation and the like (see generally, Scopes, *Protein Purification* (Springer-Verlag, N.Y., 1982)).

Methodology for commercial production of antibodies including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. No. 5,786,464, U.S. Pat. No. 5,888,809, U.S. Pat. No. 6,063,598, U.S. Pat. No. 6,114,148, U.S. Pat. No. 7,569,339, WO2004/050884, WO2005/019442, WO2008/012142, WO2008/107388, and WO2009/027471).

H. Nucleic Acids

The invention further provides nucleic acids encoding any of the heavy and light chains described above. Typically, a nucleic acid also encodes a signal peptide fused to the mature heavy or light chain encoded by the nucleic acid (e.g., signal peptides having amino acid sequences of SEQ ID NO:25, SEQ ID NO:26, SEQ ID NO:27, and SEQ ID NO:28; signal peptides having amino acid sequences of SEQ ID NO:30, SEQ ID NO:32, and SEQ ID NO:34 that can be encoded by SEQ ID NO:29, SEQ ID NO:31, and SEQ ID NO:33). Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

IV. Active Immunogens

An agent used for active immunization serves to induce in a patient the same types of antibody described in connection with passive immunization above (e.g., an antibody preferentially binding to ApoE(1-272) or other truncated form of ApoE over ApoE(1-299)). Agents used for active immunization can be the same types of immunogens used for generating monoclonal antibodies in laboratory animals (e.g., a peptide of 3-10 contiguous amino acids from the C-terminus of a desired truncated fragment, such as ApoE(1-272). Some examples of fragments that can be used include ApoE 270-272, 269-272, 268-272, 267-272, 266-272, 265-272, 264-272, and 263-272 with 268-272 and 267-272 being preferred.

The heterologous carrier and adjuvant, if used may be the same as used for generating monoclonal antibody, but may also be selected for better pharmaceutical suitability for use in humans. Suitable carriers include serum albumins, keyhole limpet hemocyanin, immunoglobulin molecules, thyroglobulin, ovalbumin, tetanus toxoid, or a toxoid from other pathogenic bacteria, such as diphtheria (e.g., CRM197), *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-S-glycerine cysteine (Pam$_3$Cys), mannan (a mannose polymer), or glucan (a β 1→2 polymer)), cytokines (e.g., IL-1, IL-1 alpha and β peptides, IL-2, γ-INF, IL-10, GM-CSF), and chemokines (e.g., MIP1-α and β, and RANTES). Immunogens may be linked to the carriers with or without spacers amino acids (e.g., gly-gly). Additional carriers include virus-like particles. Virus-like particles (VLPs), also called pseudovirions or virus-derived particles, represent subunit structures composed of multiple copies of a viral capsid and/or envelope protein capable of self assembly into VLPs of defined spherical symmetry in vivo. (Powilleit, et al., (2007) PLoS ONE 2(5):e415.) Alternatively, peptide immunogens can be linked to at least one artificial T-cell epitope capable of binding a large proportion of MHC Class II molecules., such as the pan DR epitope ("PADRE"). PADRE is described in U.S. Pat. No. 5,736,142, WO 95/07707, and Alexander J et al, Immunity, 1:751-761 (1994). Active immunogens can be presented in multimeric form in which multiple copies of an immunogen and/or its carrier are presented as a single covalent molecule.

Fragments are often administered with pharmaceutically acceptable adjuvants. The adjuvant increases the titer of induced antibodies and/or the binding affinity of induced antibodies relative to the situation if the peptide were used alone. A variety of adjuvants can be used in combination with an immunogenic fragment of ApoE, to elicit an immune response. Preferred adjuvants augment the intrinsic response to an immunogen without causing conformational changes in the immunogen that affect the qualitative form of the response. Preferred adjuvants include aluminum salts, such aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in *Vaccine Design: The Subunit and Adjuvant Approach* (eds. Powell & Newman, Plenum Press, N.Y., 1995); U.S. Pat. No. 5,057,540), (Aquila BioPharmaceuticals, Framingham, Mass.; now Antigenics, Inc., New York, N.Y.). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Another adjuvant is CpG (WO 98/40100). Adjuvants can be administered as a component of a therapeutic composition with an active agent or can be administered separately, before, concurrently with, or after administration of the therapeutic agent.

Analogs of natural fragments of ApoE that induce antibodies against ApoE(1-272) can also be used. For example, one or more or all L-amino acids can be substituted with D amino acids in such peptides. Also the order of amino acids can be reversed (retro peptide). Optionally a peptide includes all D-amino acids in reverse order (retro-inverso peptide). Peptides and other compounds that do not necessarily have a significant amino acid sequence similarity with ApoE peptides but nevertheless serve as mimetics of ApoE peptides and induce a similar immune response. Anti-idiotypic antibodies against monoclonal antibodies to ApoE as described above can also be used. Such anti-Id antibodies mimic the antigen and generate an immune response to it (see Essential Immunology, Roit ed., Blackwell Scientific Publications, Palo Alto, Calif. 6th ed., p. 181).

Peptides (and optionally a carrier fused to the peptide) can also be administered in the form of a nucleic acid encoding the peptide and expressed in situ in a patient. A nucleic acid segment encoding an immunogen is typically linked to regulatory elements, such as a promoter and enhancer that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector.

The DNA can be delivered in naked form (i.e., without colloidal or encapsulating materials). Alternatively a number of viral vector systems can be used including retroviral systems (see, e.g., Lawrie and Tumin, Cur. Opin. Genet. Develop. 3, 102-109 (1993)); adenoviral vectors (see, e.g., Bett et al, J. Virol. 67, 591 1 (1993)); adeno-associated virus vectors (see, e.g., Zhou et al., J. Exp. Med. 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol. 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., Human Gene Therapy 6, 325-333 (1995); Woo et al, WO 94/12629 and Xiao & Brandsma, Nucleic Acids. Res. 24, 2630-2622 (1996)).

DNA encoding an immunogen, or a vector containing the same, can be packaged into liposomes. Suitable lipids and related analogs are described by U.S. Pat. No. 5,208,036, U.S. Pat. No. 5,264,618, U.S. Pat. No. 5,279,833, and U.S. Pat. No. 5,283,185. Vectors and DNA encoding an immunogen can also be adsorbed to or associated with particulate carriers, examples of which include polymethyl methacrylate polymers and polylactides and poly(lactide-co-glycolides), (see, e.g., McGee et al., J. Micro Encap. 1996).

V. Screening Methods

Antibodies can be initially screened for the intended binding specificity as has already been described (e.g., preferential binding to ApoE(1-272) over ApoE(1-299)). Active immunogens can likewise be screened for capacity to induce antibodies with such binding specificity. In this case, an active immunogen is used to immunize a laboratory animal and the resulting sera tested for the appropriate binding specificity.

Antibodies having the desired binding specificity can then be tested in cellular and animal models. Cellular models include cells naturally expressing ApoE or transfected with DNA encoding ApoE(1-299) or a truncated fragment thereof, particularly ApoE(1-272). The cells used for such screening are preferentially neuronal cells. Cells can be screened for reduced levels of ApoE(1-272) (e.g., by Western blotting or immunoprecipitation of cell extracts) or reduced toxicity attributable to ApoE(1-272) as described in the Examples. Antibodies or active immunogens can also be screened in transgenic animal models of diseases associated with ApoE4. Such transgenic animals can include a human ApoE and/or human APP transgene among others, such as tau, presenilin or alpha synuclein. Such transgenic animals are disposed to develop at least one sign or symptom of a disease associated with ApoE. Numerous transgenic mice with human ApoE transgenes have been described in the scientific literature, varying in e.g., the allele expressed, knock-out of endogenous alleles, full-length ApoE transgene or a truncated fragment (e.g., ApoE(1-272)), selection of promoter, among other factors (see world wide web alzforum.org/res/com/tra), Buttini et al., J. Neurosci. 22, 10539-10548 (2002), Holtzman et al., PNAS 97, 2892-2897 (2000), Tesseur et al., Am. J. Path. 157, 1495-1510 (2000) Raffai et al., Circulation 102: II-150 (abstr.) (2000); Raffai et al., J. Biol. Chem. 277: 11064-11068 (2002). Features of Alzheimer's pathology in these models include reduced numbers of presynaptic terminals, increased plaque deposition (in models expressing both ApoE and APP), increased tau phosphorylation, impaired learning and memory and altered long term potentiation, significant learning impairment that can be assessed using a water maze (see Marley et al., PNAS 103, 5644-5651 (2006)). The activity of antibodies or active agents can be assessed by various criteria including reduction in ApoE truncated fragments, particularly ApoE(1-272), reduction in other pathological characteristics, such as amyloid deposits of $A\beta$, and inhibition or delay or behavioral deficits. Active immunogens can also be tested for induction of antibodies in the sera. Both passive and active immunogens can be tested for passage of antibodies across the blood brain barrier into the brain of a transgenic animal. Tests on an antibody or active agent are usually performed in conjunction with a control in which a parallel experiment is conducted except that the antibody or active agent is absent (e.g., replaced by vehicle). Any of the following ApoE4 antibodies (15D2, 12D3, 7C8 and 2G3), ApoE3 antibodies (12E5, 12H5 and 6H6), 2C11 (recognizes both ApoE3 and ApoE4) and 5F6 (recognizes ApoE but not otherwise characterized) among others can be used as controls. Reduction, delay or inhibition of signs or symptoms disease attributable to an antibody or active agent under test can then be assessed relative to the control.

VI. Patients Amenable to Treatment

The presence of an ApoE4 allele has been associated with increased risk, increased severity and/or earlier age of onset of a large number of neurological disease and conditions including Alzheimer's disease, Down's syndrome, mild cognitive impairment, vascular amyloid disease (e.g., cerebral amyloid angiopathy), Parkinson's disease and other Lewy body disorders, heat trauma, stroke, complications of coronary bypass surgery, amyotrophic lateral sclerosis, multiple sclerosis, diabetic neuropathy, sleep disorders, and CNS ischemia (see, e.g., Mayley et al., PNAS 103, 5644-5651 (2006)). Because of the widespread association between neurological diseases and conditions and an ApoE4 allele, the present regimes can be used in treatment or prophylaxis of any subject that is carrier of an ApoE4 allele having any neurological disease or considered at risk of developing one. The present regimes can also be used for treatment or prophylaxis in any of the above-mentioned diseases or others associated with an ApoE4 allele or elevated levels of ApoE1-272 on individuals regardless of ApoE4 carrier status. The present methods are particularly suitable for treatment or prophylaxis of Alzheimer's disease, and especially in patients who are ApoE4 carriers.

Patients amenable to treatment include individuals at risk of disease but not showing symptoms, as well as patients presently showing symptoms. Patients at risk of disease include those having a known genetic risk of a disease. Such individuals include those having relatives who have experienced this disease, and those whose risk is determined by analysis of genetic or biochemical markers. Genetic markers of risk include particularly the ApoE4 allele in heterozygous and even more so in homozygous form. Other markers of risk of Alzheimer's disease include mutations in the APP gene, particularly mutations at position 717 and positions 670 and 671 referred to as the Hardy and Swedish mutations respectively, mutations in the presenilin genes, PS1 and PS2, a family history of AD, hypercholesterolemia or atherosclerosis. Individuals presently suffering from Alzheimer's disease can be recognized by PET imaging, from characteristic dementia, as well as the presence of risk factors described above. In addition, a number of diagnostic tests are available for identifying individuals who have AD. These include measurement of CSF tau and $A\beta42$ levels. Elevated tau and decreased $A\beta42$ levels signify the presence of AD. Some mutations associated with Parkinson's disease. Ala30Pro or Ala53, or mutations in other genes associated with Parkinson's disease such as leucine rich repeat kinase, PARKS.

Individuals can also be diagnosed with any of the neurological diseases mentioned above by the criteria of the DSM IV TR.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

VII. Pharmaceutical Compositions and Methods of Treatment

In prophylactic applications, an antibody or agent for inducing an antibody or a pharmaceutical composition the same is administered to a patient susceptible to, or otherwise at risk of a disease (e.g., Alzheimer's disease) in regime (dose, frequency and route of administration) effective to reduce the risk, lessen the severity, or delay the onset of at least one sign or symptom of the disease. In particular, the regime is preferably effective to inhibit or delay accumulation of ApoE(1-272) in the brain, and/or inhibit or delay its toxic effects and/or inhibit/or delay development of behavioral deficits. In therapeutic applications, an antibody or agent to induce an antibody is administered to a patient suspected of, or already suffering from a disease (e.g., Alzheimer's disease) in a regime (dose, frequency and route of administration) effective to ameliorate or at least inhibit further deterioration of at least one sign or symptom of the disease. In particular, the regime is preferably effective to reduce or at least inhibit further increase of levels of ApoE(1-272), associated toxicities and/or behavioral deficits.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the $p<0.05$ or $0.01$ or even $0.001$ level.

Effective doses of vary depending upon many different factors, including means of administration, target site, physiological state of the patient, whether the patient is an ApoE carrier, whether the patient is human or an animal, other medications administered, and whether treatment is prophylactic or therapeutic.

An exemplary dosage range for antibodies is from about 0.01 to 5 mg/kg, and more usually 0.1 to 3 mg/kg or 0.15-2 mg/kg or 0.15-1.5 mg/kg, of patient body weight. Antibody can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

The amount of an agent for active administration varies from 0.1-500 µg per patient and more usually from 1-100 or 1-10 µg per injection for human administration. The timing of injections can vary significantly from once a day, to once a year, to once a decade. A typical regimen consists of an immunization followed by booster injections at time intervals, such as 6 week intervals or two months. Another regimen consists of an immunization followed by booster injections 1, 2 and 12 months later. Another regimen entails an injection every two months for life. Alternatively, booster injections can be on an irregular basis as indicated by monitoring of immune response.

Antibodies or agents for inducing antibodies are preferably administered via a peripheral route (i.e., one in which an administered or induced antibody crosses the blood brain barrier to reach an intended site in the brain. Routes of administration include topical, intravenous, oral, subcutaneous, intraarterial, intracranial, intrathecal, intraperitoneal, intranasal or intramuscular. Preferred routes for administration of antibodies are intravenous and subcutaneous. Preferred routes for active immunization are subcutaneous and intramuscular. This type of injection is most typically performed in the arm or leg muscles. In some methods, agents are injected directly into a particular tissue where deposits have accumulated, for example intracranial injection.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The present regimes can be administered in combination with another agent effective in treatment or prophylaxis of the disease being treated. For example, in the case of Alzheimer's disease, the present regimes can be combined with immunotherapy against Aβ (WO/2000/072880), cholinesterase inhibitors or memantine or in the case of Parkinson's disease immunotherapy against alpha synuclein WO/2008/103472, Levodopa, dopamine agonists, COMT inhibitors, MAO-B inhibitors, Amantadine, or anticholinergic agents.

EXAMPLES

Example 1

Antibody Preparation

To prepare antibodies specific for the neo-epitope of ApoE ending at 272 CGG-LVEDM (SEQ ID NO:5); ApoE 268-272 (LVEDM; SEQ ID NO:41) with an artificial CGG added as linker and for ease of coupling) was conjugated to Sheep anti Mouse IgG(H+L) using EMCS ([N-e-Maleimidocaproyloxy]succinimide ester) which allows the cross-linking of the free amines on the sheep anti mouse to the cysteine on the peptide.

Five A/J mice were immunized on day 0 with 100 µg of the peptide conjugate in Freund's Complete Adjuvant, and again on day 14, 28 and 56 with 100 µg of peptide in Freund's Incomplete Adjuvant. On day 63 mice were bled via a tail vein nick and dilutions of serum were then used to determine antibody titers to the CGG-LVEDM peptide (SEQ ID NO:5). All animals raised an acceptable titer.

Animal #5 had a titer of 218000 and was chosen for fusion. Fusion was done using a modification of the method of Kohler and Milstein. Fused cells were incubated overnight in selection media, viable cells counted and resuspended in CloneMedia for Hybridomas from Genetix at approximately 5000 cells/well with the addition of azaserine for selection of fused cells, mIL6 to promote growth, and CGG-LVEDM (SEQ ID NO:5) coupled to activated ovalbumin then fluorescently labeled to image positive clones.

Initial selection was done using ClonePix-FL software. Colonies deemed positive by our criteria were transferred to 96 well plates, allowed to grow to 50-80% confluence and rescreened for binding to CGG-LVEDM (SEQ ID NO:5) and no binding to a peptide that spans aa 266-276 of ApoE (EPLVEDMQRQW; SEQ ID NO:6). Antibodies that met this criteria and showed good stability were cloned and expanded to purify the antibody from tissue culture media.

Antibodies can also be tested for binding to ApoE(1-272). The ApoE(1-272) fragment can be any of the ApoE2, E3 or E4 isoforms. Such a fragment is preferably recombinantly expressed. Binding can be assessed by immunoprecipitation and/or western blots. Antibodies can also be tested by immunohistochemistry on AD brain tissue from Apo E2, E3 or E4 carriers compared with controls to see if a given antibody is specific for the appropriate fragments.

Example 2

In Vitro Testing of Antibodies

Neuro 2A cells (mouse neuroblast from neuroblastoma, ATCC; Cat. No. CCL-131) expressing transfected human ApoE4 process it to the 1-272 fragment which exerts neurotoxicity at a number of levels (as detected by a simple 3-(4,5-demithylthiazol-2-yl)-2,5-diphenyltrazolium bromide (MTT) assay for instance (see Chang et al., PNAS 102, 18694-18699 (2005)). MTT is a yellow tetrazolium salt reduced in metabolically active cells to form insoluble purple formazan crystals, which are solubilized by the addition of a detergent. The color can then be quantified by spectrophotometric means. These cells can be used to determine whether ApoE(1-272)-specific anti-Apo E antibodies block the toxicity of the fragment in this neuronal cell line. Antibody uptake if needed can occur by a mechanism such as micropinocytosis or pinocytosis. A read-through antibody (i.e., antibody with an epitope bridging the site of truncation) can be used as a negative control. A positive outcome is increased MTT signal in antibody treated cells relative to untreated controls (negative control) or similar signal relative to untransfected cells (positive control) (i.e., preservation of metabolic activity).

A similar assay can be performed with Neuro2A cells transfected with ApoE(1-272). These cells produce the ApoE1-272 truncated fragment directly without proteolytic process.

Example 3

In Vivo Testing of Antibodies

Antibodies preferentially binding to ApoE(1-272) over ApoE(1-299) or agents inducing such antibodies can be administered to human ApoE4 containing mice on an APP transgenic background. Holtzman et al., PNAS 2000 vol. 97 no. 6 2892-2897 described an example of such mice in which mice having a knocked out endogenous Apo alleles are transfected with human APP V717F and human ApoE4. Immunohistological staining of the transgenic mouse brain and western blots of these mice show increased levels of ApoE(1-272) fragment in the absence of such treatment and leads to behavioral deficits in the mice. Reduced levels of ApoE (1-272), increased synaptophysin levels, or inhibition of behavioral deficits can therefore be used as efficacy endpoints.

Example 4

Immunoprecipitation Blotting

Solutions and Reagents:

The following solutions were prepared with Milli-Q or equivalently purified water: (1) 1× Phosphate Buffered Saline (PBS); (2) 1× Cell Lysis Buffer: 20 mM Tris (pH 7.5), 150 mM NaCl, 1 mM EDTA, 1 mM EGTA, 1% Triton X-100, 2.5 mM Sodium pyrophosphate, 1 mM β-glycerophosphate, 1 mM Na3VO4, 1 µg/ml Leupeptin. 1 mM PMSF was added to the cell lysis buffer immediately prior to use; and (3) 3×SDS Sample Buffer: 187.5 mM Tris-HCl (pH 6.8 at 25° C.), 6% w/v SDS, 30% glycerol, 150 mM DTT, 0.03% w/v bromophenol blue. Protein G Agarose Beads were used for immunoprecipitation.

Cell Lysates Preparation:

Media was aspirated. Cells were treated for desired time by adding fresh media containing regulator. Media was then removed and cells rinsed with ice-cold PBS to harvest cells under nondenaturing conditions. PBS was removed, and 0.5 ml ice-cold 1× cell lysis buffer was added to each plate (10 cm). The plates were incubated on ice for 5 minutes. Cells were scraped off the plates and transferred to microcentrifuge tubes. The cells were kept on ice, and sonicated on ice three times for 5 seconds each. The samples were then microcentrifuged for 10 minutes at 14,000×g, 4° C., and the supernatant was transferred to a new tube. When necessary, lysate was stored at −80° C.

Immunoprecipitation and Blotting:

A lysate pre-clearing step was performed to reduce nonspecific binding to the Protein A/G agarose beads. Specifically, 20 µl agarose beads slurry was added to 250 µl cell lysate. The mixture was incubated at 4° C. for 30 minutes, and spun at maximum speed for 2 minutes. The supernatant was recovered for antibody in next step.

About 250 µl cell lysate was mixed with 5 µg of primary antibody 15G8. The mixture was incubated with gentle rocking overnight at 4° C. Protein G agarose beads (20 µl of 50% bead slurry) was then added and the mixture was incubated with gentle rocking for another 1-3 hours at 4° C. The sample was microcentrifuged for 30 seconds at 4° C. Pellet was washed five times with 500 µl of 1× cell lysis buffer. The sample was kept on ice during washes.

The pellet was resuspended with 20 µl 3×SDS sample buffer. The resuspended pellet was vortexed, and then microcentrifuged for 30 seconds. The sample was heated to 95-100° C. for 2-5 minutes and microcentrifuged for 1 minute at 14,000×g. About 15-30 µA sample was loaded on SDS-PAGE gel (12-15%). The electrophoresis was carried out at 150 Volts. The SDS-PAGE gel was electrotransferred to a nitrocellulose membrane. The membrane was incubated in 25 ml of blocking buffer for 1 hour at room temperature, and washed three times for minutes each with 15 ml of TBS/T.

The membrane was then incubated with primary antibody anti-ApoE4 antibody 1F9 (MBL International Corp., Cat# M067-3) in 10 ml primary antibody dilution buffer with gentle agitation overnight at 4° C. The membrane was then washed three times for 5 minutes each with 15 ml of TBS/T. Afterwards, the membrane was incubated with 10 ml Goat anti-Mouse IgG_IRDye 800CW antibody (Li-cor Bio #926-32210) 1:20000 in dilution buffer with gentle agitation for 1 hour at room temperature, and washed three times for 5 minutes each with 15 ml of TBS/T. The membrane was scanned using Li-Cor Odyssey Imager.

Lysates of full-length ApoE3, full-length ApoE4, ApoE3 (1-272), and ApoE4(1-272) lysates were detected using Western blot with 1 µg/ml 1F9 (Medical and Biological Laboratories) (Lanes 1-4; FIG. 3). In addition, lysates of full-length ApoE3, full-length ApoE4, ApoE3(1-272), and ApoE4 (1-272) were immununoprecipitated with m15G8 antibody. The m15G8 immunoprecipitation were then detected using Western blot with 1 µg/ml 1F9 (Lanes 5-8; FIG. 3). 1F9 is a ApoE4-specific antibody that does not bind ApoE3 proteins (FIG. 3; Lanes 1, 2, 5, and 6). The results were shown in FIG. 3: Lane 1: Full-length ApoE3 lysate; Lane 2: ApoE3 1-272 lysate; Lane 3: Full-length ApoE4 lysate; Lane 4: ApoE4 1-272 lysate; Lane 5: Full-length ApoE3 immunoprecipitated with mouse 15G8; Lane 6: ApoE3 1-272 immunoprecipitated with mouse 15G8; Lane 7: Full-length ApoE4 immunoprecipitated with mouse 15G8; Lane 8: ApoE4 1-272 immunoprecipitated with mouse 15G8.

The m15G8 immunoprecipitation of ApoE4 (1-272) was detected by 1F9 (Lane 8; FIG. 3). However, blotting with 1F9 fails to detect any m15G8 immunoprecipitation of full-length ApoE4 (Lane 7; FIG. 3). These results demonstrate that 15G8 is specific for 1-272.

Example 5

Characterization of 12C12, 15E10, and 15G8 by Western Blot

Figure 4:
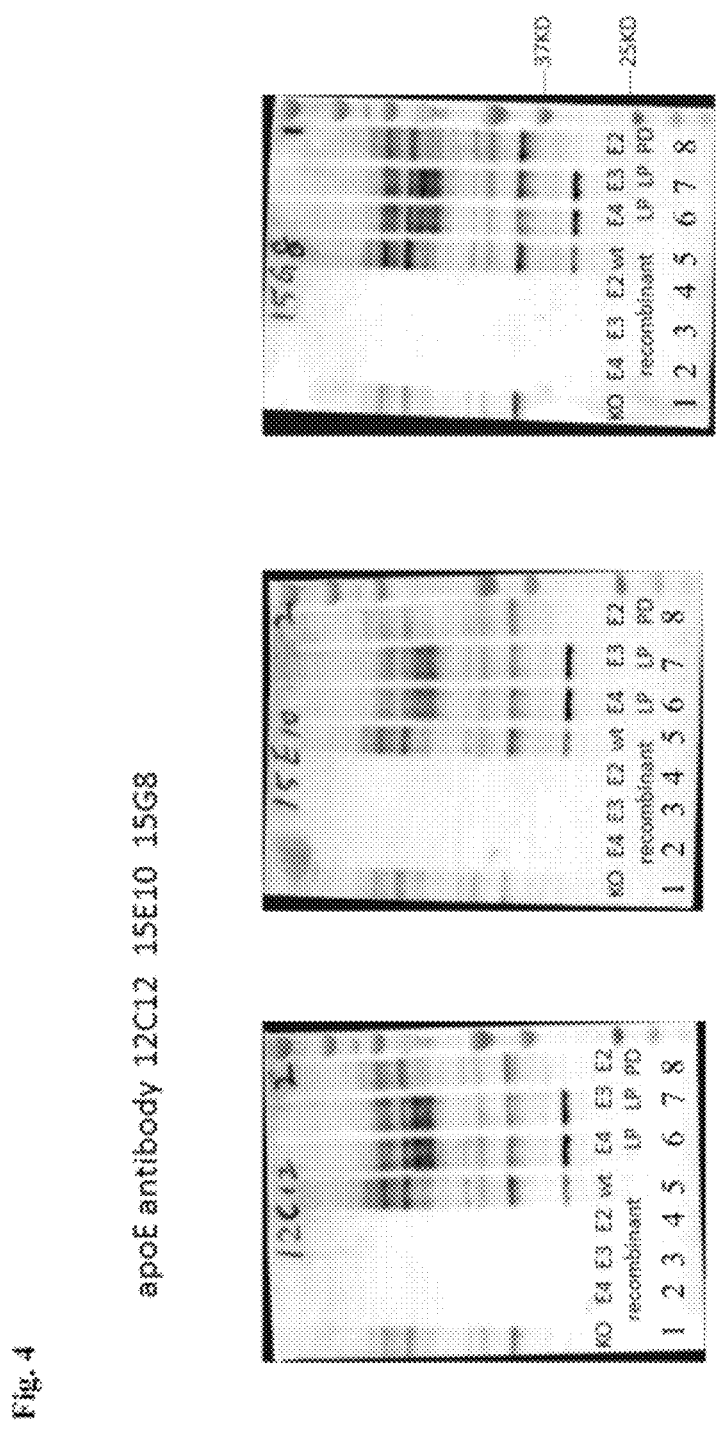

Cortical tissue lysates from wild-type mouse, ApoE KO mouse, and transgenic mice that express human ApoE isoform knock-in (E2, E3, and E4 strains) and human Amyloid beta were analyzed using western blot. Monoclonal antibodies 12C12, 15E10, and 15G8 recognize multiple bands in tissue lysates of different strains, including apoE KO mouse which serve as negative control/background reactivity of the mAbs (FIG. 4). The results were shown in FIG. 4: Lane 1: western blot of cortical lysates from apoE KO mouse; Lane 2: recombinant full length ApoE4; Lane 3: recombinant full length ApoE3; Land 4: recombinant full length ApoE2; Lane 5: western blot of cortical lysates from wild-type mouse; Lane 6: western blot of cortical lysates from transgenic E4 knock-in mouse; Lane 7: western blot of cortical lysates from transgenic E3 knock-in mouse; Lane 8: western blot of cortical lysates from transgenic E2 knock-in mouse.

In cortical lysates of wild-type, E3 or E4 knock-in mouse (but not in cortical lysates of E2 or ApoE KO mouse), all three antibodies recognize a band around 30 KDa (Lanes 5, 6, and 7). In cortical lysates from E3 or E4 knock-in mouse (but not in tissue lysates of wild-type, E2 knock-in, or ApoE KO mouse), all three antibodies recognize a band around 60 KDa (Lanes 6 and 7). The molecular weights of these bands specific to wild-type, E3 and E4 knock-in cortical lysates are consistent with those of ApoE(1-272) monomer (31.5 KDa) and dimer (63 KDa) (FIG. 4).

Example 6

Design of Humanized 15G8 Antibodies

The starting point or donor antibody for humanization is the mouse antibody 15G8. The variable kappa (Vκ) of m15G8 belongs to mouse Kabat subgroup 2 which corresponds to human Kabat subgroup 2. The VH of m15G8 belongs to mouse Kabat subgroup 3d which corresponds to human Kabat subgroup 3 (Kabat et al., Sequences of Proteins of Immunological Interest, Fifth Edition. NIH Publication No. 91-3242, 1991). Kabat numbering is used throughout in this Example.

The 16-residue CDR-L1 belongs to canonical class 4, the 7-residue CDR-L2 belongs to class 1, the 9-residue CDR-L3 belongs to class 1 in Vk (Martin & Thornton, J Mol Biol. 263:800-15, 1996). The 5-residue CDR-H1 belongs to class 1, the 16-residue CDR-H2 belongs to class 3 (Martin & Thornton, J Mol. Biol. 263:800-15, 1996). CDR-H3 has no canonical classes. The residues at the interface between the VK and VH domains are the ones commonly found.

A search was made over the protein sequences in the PDB database (Deshpande et al., Nucleic Acids Res. 33: D233-7, 2005) to find structures that would provide a rough structural model of 15G8. The crystal structure of dimeric antibody 4-B8(8)/E9 (pdb code 1KFA; Murata et al, Biochem. Biophys. Res. Commun. 293:489-496, 2002) was chosen for the Vh structure since it has good overall sequence similarity and reasonable resolution (2.8 Å). In addition, CDRs-H1 and H2 of 1KFA have the same canonical structures as those of m15G8 Vh. 1KFA has an insertion in CDR-H3 at 100D position. The crystal structure of Nq16-113.8 (pdb code 2CJU_L; Scotti & Gherardi, J. Mol. Biol., 359:1161, 2006) was chosen for the Vk structure since it had good overall sequence similarity and reasonably good resolution (2.5 Å). Additionally, CDRs-L1, L2 and L3 had the same canonical structures as m15G8 Vk. A structural model of the mouse 15G8 Fv region was built using the 1KFA and 2CJU structures as templates in the PRIME modeling workflow (PSP 3.0111) within Schrodinger Suite2011 (update release, September 2012). The structural model for CDR3 of the heavy chain was further refined by Schrodinger loop search for the region comprising residues 99-107. Ten iterations of extended loop sampling yielded one energetically preferred loop conformation in the context of the whole Fv region.

A search of the non-redundant protein sequence database from NCBI allowed selection of suitable human frameworks into which to graft the murine CDRs. For Vk, a human kappa light chain with GenBank accession code AAT86035 (GI: 50898163) was chosen. It belongs to Kabat human kappa subgroup 2 and has the same canonical classes for CDR-L1, L2 and L3 as those of m15G8. For Vh, human Ig heavy chain AAX82494 (GI: 62421461) (Lundquist et al, Infect. Immun. 74 (6), 3222-3231, 2006) was chosen. It belongs to Kabat human heavy subgroup 3 and has the same canonical classes for CDR-H1 and H2 as those of m15G8. CDR-H3 of 15G8 has no canonical class.

```
> AAX82494_VH_HuFwr
                                                 (SEQ ID NO: 7)
QVQLQESGGGLVKPGGSLKLSCAASGFTFSSYGMSWVRQTPDKRLEWVATISSGGSYT

YYPDSVKGRFTISRDNAKNTLYLQMSSLKSEDTAMYYCARLYYGYRYYFDYWGQGTM

VTVSS
```

> AAT86035_VL_HuFwr
(SEQ ID NO: 8)
DVVMTQSPLSLPVTLGQPASISCRSSQSLLHSDGNTYLLWFLQRPGQSPRRLLYKVSDRD

SGVPDRFSGSGSGTDFTLKISRVEAEDVGVYYCMQGTHWPWTFGQGTKVEIK

The rationales for selection of several positions as candidates for backmutation are as follows.
Variable Light Chain Backmutations:
V3L (here as elsewhere for framework backmutations, the first mentioned residue is the human residue and the second the mouse residue): In the structure model, Leucine in this position packs close to the CDR and there is a high probability that this residue makes a contact with antigen. Therefore we make this back mutation.

F36Y: This is an interface residue. In the structure model, this residue is in close contact with heavy chain W103 interface residue. Therefore we make this back mutation.

R46L: This is an interface residue. In the structure model, Leu packs beneath CDRL2 and CDRH3, replacement with Arg will distort the conformation of these two CDRs.
Variable Heavy Chain Backmutations:
Q1E, Q3K & Q5V: In the structure model, Lysine at Kabat position H3 is in contact with CDRH1. In the structure, these three residues pack together, i.e., both Glu at Kabat position H1 and Val at Kabat position H5 interact with Lysine at Kabat position H3. Therefore these three residues are back mutated together.

D42E: Glu at Kabat position H42 is a more frequent residue in human frameworks at this position than Aspartate, therefore it is back mutated.

K83R: Arg is more frequent in human frameworks at Kabat position H83, therefore it is back mutated.

Two humanized heavy chains and two humanized light chains were made incorporating various back mutations (FIGS. 1-2 and Tables 1-2). The amino acids at L3, L36, L46, H1, H3, H5, H42, and H83 in Hu15G8VLv1-v2 and Hu15G8VHv1-v2 are listed in Tables 3-4.

TABLE 1

VH Backmutations

| VH variant | VH exon acceptor sequence | donor framework residues |
|---|---|---|
| Hu15G8VHv1 SEQ ID NO: 11 | AAX82494 SEQ ID NO: 7 | H1, H3, H5, H42, H83 |
| Hu15G8VHv2 SEQ ID NO: 17 | AAX82494 SEQ ID NO: 7 | none |

TABLE 2

VL Backmutations

| VL variant | VL exon acceptor sequence | donor framework residues |
|---|---|---|
| Hu15G8VLv1 SEQ ID NO: 14 | AAT86035 SEQ ID NO: 8 | L3, L36, L46, |
| Hu15G8VLv2 SEQ ID NO: 18 | AAT86035 SEQ ID NO: 8 | none |

>15G8vh Version1
Amino acid sequence:
(SEQ ID NO: 11)
EVKLVESGGGLVKPGGSLKLSCAASGFTFSFYAMSWVRQTPEKRLEWVASLSRGGSTY

YPDSVKGRFTISRDNAKNTLYLQMSSLRSEDTAMYYCAREGATALYAMDYWGQGTM

VTVSS

Nucleic acid sequence:
(SEQ ID NO: 12)
GAGGTGAAGCTGGTGGAGTCCGGCGGCGGCCTGGTGAAGCCCGGCGGCTCCCTGAA

GCTGTCCTGCGCCGCCTCCGGCTTCACCTTCTCCTTCTACGCCATGTCCTGGGTGCGC

CAGACCCCCGAGAAGCGCCTGGAGTGGGTGGCCTCCCTGTCCCGCGGCGGCTCCAC

CTACTACCCCGACTCCGTGAAGGGCCGCTTCACCATCTCCCGCGACAACGCCAAGAA

CACCCTGTACCTGCAGATGTCCTCCCTGCGCTCCGAGGACACCGCCATGTACTACTG

CGCCCGCGAGGGCGCCACCGCCCTGTACGCCATGGACTACGGGGCCAGGGCACCA

TGGTGACCGTGTCCTCC

>15G8Vκ Version1
Amino acid sequence:
(SEQ ID NO: 14)
DVLMTQSPLSLPVTLGQPASISCRSSQSIVHSNGNTYLQWYLQRPGQSPRLLLYKVSNR

FSGVPDRFSGSGSGTDFTLKISRVEAEDVGVYYCFQGSHVPWTFGQGTKVEIK

```
Nucleic acid sequence:
                                                       (SEQ ID NO: 15)
GACGTGCTGATGACCCAGTCCCCCCTGTCCCTGCCCGTGACCCTGGGCCAGCCCGCC

TCCATCTCCTGCCGCTCCTCCCAGTCCATCGTGCACTCCAACGGCAACACCTACCTG

CAGTGGTACCTGCAGCGCCCCGGCCAGTCCCCCCGCCTGCTGCTGTACAAGGTGTCC

AACCGCTTCTCCGGCGTGCCCGACCGCTTCTCCGGCTCCGGCTCCGGCACCGACTTC

ACCCTGAAGATCTCCCGCGTGGAGGCCGAGGACGTGGGCGTGTACTACTGCTTCCA

GGGCTCCCACGTGCCCTGGACCTTCGGCCAGGGCACCAAGGTGGAGATCAAG

>15G8vh Version2 (No backmutation)
                                                       (SEQ ID NO: 17)
QVQLQESGGGLVKPGGSLKLSCAASGFTFS*FYAMS*WVRQTPDKRLEWVA*SLSRGGSTY*

*YPDSVKG*RFTISRDNAKNTLYLQMSSLKSEDTAMYYCAR*EGATALYAMDY*WGQGTMV

TVSS

>15G8Vκ Version2 (No backmutation)
                                                       (SEQ ID NO: 18)
DVVMTQSPLSLPVTLGQPASISC*RSSQSIVHSNGNTYLQ*WFLQRPGQSPRRLLY*KVSNRF*

*S*GVPDRFSGSGSGTDFTLKISRVEAEDVGVYYC*FQGSHVPWT*FGQGTKVEIK
```

TABLE 3

Kabat numbering of preferred framework residues for backmutation in humanized 15G8 antibody heavy chains

| | AAX82494 SEQ ID NO: 7 | mouse 15G8 heavy chain SEQ ID NO: 9 | Hu15G8VH1 SEQ ID NO: 11 | Hu15G8VH2 SEQ ID NO: 17 |
|---|---|---|---|---|
| H1 | Q | E | E | Q |
| H3 | Q | K | K | Q |
| H5 | Q | V | V | Q |
| H42 | D | E | E | D |
| H83 | K | R | R | K |

TABLE 4

Kabat numbering of preferred framework residues for backmutation in humanized 15G8 antibody light chains

| | AAT86035 SEQ ID NO: 8 | Mouse 15G8 light chain SEQ ID NO: 10 | Hu15G8VL1 SEQ ID NO: 14 | Hu15G8VL2 SEQ ID NO: 18 |
|---|---|---|---|---|
| L3 | V | L | L | V |
| L36 | F | Y | Y | F |
| L46 | R | L | L | R |

All publications (including GenBank Accession numbers, UniProtKB/Swiss-Prot accession numbers and the like), patents and patent applications cited are herein incorporated by reference in their entirety for all purposes to the same extent as if each individual publication, patent and patent application was specifically and individually indicated to be incorporated by reference in its entirety for all purposes. In the event of any variance in sequences associated with Genbank and UniProtKB/Swiss-Prot accession numbers and the like, the application refers to the sequences associated with the cited accession numbers as of the filing date of the application.

What is claimed is:

1. A monoclonal antibody that preferentially binds to ApoE (1-272) relative to binding to ApoE(1-299), wherein the antibody is a humanized, chimeric, veneered or human antibody that binds to an epitope including a free carboxyl group of position 272 of ApoE(1-272).

2. The monoclonal antibody of claim 1 that binds to an epitope including residue 272 of ApoE(1-272).

3. A monoclonal antibody comprising three light chain Kabat CDRs designated as SEQ ID NO:22, SEQ ID NO:23, and SEQ ID NO:24, and three heavy chain CDRs designated as SEQ ID NO:19, SEQ ID NO:20, and SEQ ID NO:21.

4. The antibody of any of claim 1, 2 or 3, wherein the antibody competes for specific binding to ApoE with 15G8 and the heavy chain constant region is of human IgG1m1 or IgG1m3 allotype.

5. The antibody of any of claim 1, 2 or 3, wherein the antibody binds to the same epitope on ApoE as 15G8 and the heavy chain constant region is of human Ig1m1 or IgG1m3 allotype.

6. The antibody of claim 1, wherein the antibody competes for specific binding to ApoE with 15G8, wherein 15G8 is a mouse IgG1 kappa antibody having a heavy chain variable region of SEQ ID NO:9 and a light chain variable region of SEQ ID NO:10.

7. The antibody of claim 6, wherein the antibody binds to the same epitope on ApoE as 15G8.

8. The monoclonal antibody of claim 1 wherein the antibody is an Fab fragment, single chain Fv, or single domain antibody.

9. The monoclonal antibody of claim 8, comprising at least one mutation in the constant region.

10. The monoclonal antibody of claim 1, wherein the isotype is human IgG1.

11. The monoclonal antibody of claim 1, wherein the isotype is human IgG2 or IgG4 isotype.

12. The antibody of claim 1, wherein the heavy chain constant region is a mutant form of natural human constant region which has reduced binding to an Fcγ receptor relative to the natural human constant region.

13. A pharmaceutical composition comprising a monoclonal antibody that preferentially binds to ApoE(1-272) relative to binding to ApoE(1-299)), wherein the antibody is a humanized, chimeric, veneered or human antibody that binds to an epitope including a free carboxyl group of position 272 of ApoE(1-272) and a pharmaceutically acceptable carrier.

14. The pharmaceutical composition of claim 13, wherein the antibody comprises three light chain Kabat CDRs designated as SEQ ID NO:22, SEQ ID NO:23, and SEQ ID NO:24, and three heavy chain CDRs designated as SEQ ID NO:19, SEQ ID NO:20, and SEQ ID NO:21.

15. The monoclonal antibody of claim 3 wherein the antibody is a humanized, chimeric or veneered form of monoclonal antibody 15G8.

16. The antibody of claim 15, wherein the light chain variable region framework has at least 85% sequence identity to AAT86035 (SEQ ID NO:8).

17. The antibody of claim 15, wherein the light chain variable region framework has at least 96% sequence identity to AAT86035 (SEQ ID NO:8).

18. The antibody of claim 15, wherein the heavy chain variable region framework has at least 85% sequence identity to AAX82494 (SEQ ID NO:7).

19. The antibody of claim 15, wherein the heavy chain variable region framework has at least 93% sequence identity to AAX82494 (SEQ ID NO:7).

20. The antibody of claim 3, wherein the amino acid sequence of the mature heavy chain variable region is SEQ ID NO:17 and the amino acid sequence of the mature light chain variable region is SEQ ID NO:18 provided that position L3 (Kabat numbering) can be occupied by V or L, position L36 (Kabat numbering) can be occupied by F or Y, position L46 (Kabat numbering) can be occupied by R or L, position H1 (Kabat numbering) can be occupied by Q or E, position H3 (Kabat numbering) can be occupied by Q or K, position H5 (Kabat numbering) can be occupied by Q or V, position H42 (Kabat numbering) can be occupied by D or E, and position H83 (Kabat numbering) can be occupied by K or R.

21. The antibody of claim 20, wherein position L3 (Kabat numbering) is occupied by V, position L36 (Kabat numbering) is occupied by F, and position L46 (Kabat numbering) is occupied by R.

22. The antibody of claim 20, wherein position H1 (Kabat numbering) is occupied by E, position H3 (Kabat numbering) is occupied by K, position H5 (Kabat numbering) is occupied by V, position H42 (Kabat numbering) is occupied by E, and position H83 (Kabat numbering) is occupied by R.

23. The antibody of claim 20, wherein position H1 (Kabat numbering) is occupied by Q, position H3 (Kabat numbering) is occupied by Q, position H5 (Kabat numbering) is occupied by Q, position H42 (Kabat numbering) is occupied by D, and position H83 (Kabat numbering) is occupied by K.

24. The antibody of claim 20, wherein position L3 (Kabat numbering) is occupied by L, position L36 (Kabat numbering) is occupied by Y, and position L46 (Kabat numbering) is occupied by L.

25. The antibody of claim 3, comprising:
(i) a humanized heavy chain comprising the three Kabat CDRs of SEQ ID NO:17 and a mature heavy chain variable framework region having 65-85% identity to the corresponding heavy chain variable region framework of SEQ ID NO:17; and
(ii) a humanized light chain comprising the three Kabat CDRs of SEQ ID NO:18 and a mature light chain variable framework region having 65-85% identity to the corresponding light chain variable region framework of SEQ ID NO:18;
wherein position L3 (Kabat numbering) is occupied by L, and/or position L36 (Kabat numbering) is occupied by Y, and/or position L46 (Kabat numbering) is occupied by L, and/or position H1 (Kabat numbering) is occupied by E, and/or position H3 (Kabat numbering) is occupied by K, and/or position H5 (Kabat numbering) is occupied by V, and/or position H42 (Kabat numbering) is occupied by E, and/or position H83 (Kabat numbering) is occupied by R.

26. The antibody of claim 25, wherein position L3 (Kabat numbering) is occupied by L, position L36 (Kabat numbering) is occupied by Y, position L46 (Kabat numbering) is occupied by L, position H1 (Kabat numbering) is occupied by E, position H3 (Kabat numbering) is occupied by K, position H5 (Kabat numbering) is occupied by V, position H42 (Kabat numbering) is occupied by E, and position H83 (Kabat numbering) is occupied by R.

27. The antibody of claim 3, comprising:
(i) a humanized heavy chain comprising the three Kabat CDRs of SEQ ID NO:17 and a mature heavy chain variable framework region having 65-85% identity to the corresponding heavy chain variable region framework of SEQ ID NO:17; and
(ii) a humanized light chain comprising the three Kabat CDRs of SEQ ID NO:18 and a mature light chain variable framework region having 65-85% identity to the corresponding light chain variable region framework of SEQ ID NO:18;
wherein position L3 (Kabat numbering) is occupied by V, and/or position L36 (Kabat numbering) is occupied by F, and/or position L46 (Kabat numbering) is occupied by R, and/or position H1 (Kabat numbering) is occupied by Q, and/or position H3 (Kabat numbering) is occupied by Q, and/or position H5 (Kabat numbering) is occupied by Q, and/or position H42 (Kabat numbering) is occupied by D, and/or position H83 (Kabat numbering) is occupied by K.

28. The antibody of claim 27, wherein position L3 (Kabat numbering) is occupied by V, position L36 (Kabat numbering) is occupied by F, position L46 (Kabat numbering) is occupied by R, position H1 (Kabat numbering) is occupied by Q, position H3 (Kabat numbering) is occupied by Q, position H5 (Kabat numbering) is occupied by Q, position H42 (Kabat numbering) is occupied by D, and position H83 (Kabat numbering) is occupied by K.

29. The antibody of claim 3, comprising:
   (i) a humanized heavy chain comprising the three Kabat CDRs of SEQ ID NO:17 and a mature heavy chain variable framework region having 65-85% identity to the corresponding heavy chain variable region framework of SEQ ID NO:17; and
   (ii) a humanized light chain comprising the three CDRs of SEQ ID NO:18 and a mature light chain variable framework region having 65-85% identity to the corresponding light chain variable region framework of SEQ ID NO:18;
   wherein position L3 (Kabat numbering) is occupied by L, and/or position L36 (Kabat numbering) is occupied by Y, and/or position L46 (Kabat numbering) is occupied by L, and/or position H1 (Kabat numbering) is occupied by Q, and/or position H3 (Kabat numbering) is occupied by Q, and/or position H5 (Kabat numbering) is occupied by Q, and/or position H42 (Kabat numbering) is occupied by D, and/or position H83 (Kabat numbering) is occupied by K.

30. The antibody of claim 29, wherein position L3 (Kabat numbering) is occupied by L, position L36 (Kabat numbering) is occupied by Y, position L46 (Kabat numbering) is occupied by L, position H1 (Kabat numbering) is occupied by Q, position H3 (Kabat numbering) is occupied by Q, position H5 (Kabat numbering) is occupied by Q, position H42 (Kabat numbering) is occupied by D, and position H83 (Kabat numbering) is occupied by K.

31. The antibody of claim 3, comprising:
   (i) a humanized heavy chain comprising the three Kabat CDRs of SEQ ID NO:17 and a mature heavy chain variable framework region having 65-85% identity to the corresponding heavy chain variable region framework of SEQ ID NO:17; and
   (ii) a humanized light chain comprising the three CDRs of SEQ ID NO:18 and a mature light chain variable framework region having 65-85% identity to the corresponding light chain variable region framework of SEQ ID NO:18;
   wherein position L3 (Kabat numbering) is occupied by V, and/or position L36 (Kabat numbering) is occupied by F, and/or position L46 (Kabat numbering) is occupied by R, and/or position H1 (Kabat numbering) is occupied by E, and/or position H3 (Kabat numbering) is occupied by K, and/or position H5 (Kabat numbering) is occupied by V, and/or position H42 (Kabat numbering) is occupied by E, and/or position H83 (Kabat numbering) is occupied by R.

32. The antibody of claim 31, wherein position L3 (Kabat numbering) is occupied by V, position L36 (Kabat numbering) is occupied by F, position L46 (Kabat numbering) is occupied by R, position H1 (Kabat numbering) is occupied by E, position H3 (Kabat numbering) is occupied by K, position H5 (Kabat numbering) is occupied by V, position H42 (Kabat numbering) is occupied by E, and position H83 (Kabat numbering) is occupied by R.

33. The antibody of claim 3, wherein the mature heavy chain variable region has an amino acid sequence of SEQ ID NO:11 and the mature light chain variable region has an amino acid sequence of SEQ ID NO:14.

34. The antibody of claim 33, wherein the heavy chain constant region is of human IgG1m3 allotype.

35. The antibody of claim 33, wherein the mature heavy chain variable region is fused to a heavy chain constant region having the amino acid sequence of SEQ ID NO:39 provided the C-terminal lysine residue may be omitted and the mature light chain constant region is fused to a light chain constant region having the amino acid sequence of SEQ ID NO:35.

36. The antibody of claim 35, comprising a mature light chain having the amino acid sequence of SEQ ID NO:16 and a mature heavy chain having the amino acid sequence of SEQ ID NO:13.

37. The antibody of claim 33, comprising a mature heavy chain variable region having the amino acid sequence of SEQ ID NO:11, a heavy chain constant region having the amino acid sequence of SEQ ID NO:39, a mature light chain variable region having the amino acid sequence of SEQ ID NO:14 and a light chain constant region having the amino acid sequence of SEQ ID NO:35.

38. The antibody of claim 3, wherein the mature heavy chain variable region has an amino acid sequence of SEQ ID NO:17 and the mature light chain variable region has an amino acid sequence of SEQ ID NO:18.

39. The antibody of claim 38, wherein the heavy chain constant region is of human IgG1m3 allotype.

40. The antibody of claim 38, wherein the mature heavy chain variable region is fused to a heavy chain constant region having the amino acid sequence of SEQ ID NO:39 provided the C-terminal lysine residue may be omitted and the mature light chain constant region is fused to a light chain constant region having the amino acid sequence of SEQ ID NO:35.

41. The antibody of claim 38 comprising a mature heavy chain variable region having the amino acid sequence of SEQ ID NO:17, a heavy chain constant region having the amino acid sequence of SEQ ID NO:39, a mature light chain variable region having the amino acid sequence of SEQ ID NO:18 and a light chain constant region having the amino acid sequence of SEQ ID NO:35.

42. The antibody of claim 3, wherein the mature heavy chain variable region has an amino acid sequence of SEQ ID NO:17 and the mature light chain variable region has an amino acid sequence of SEQ ID NO:14.

43. The antibody of claim 3, wherein the heavy chain constant region has the amino acid sequence of SEQ ID NO:39 provided the C-terminal lysine residue may be omitted.

44. The antibody of claim 43, wherein the heavy chain constant region has the amino acid sequence of SEQ ID NO:39.

45. The antibody of claim 3, wherein the heavy chain constant region has the amino acid sequence of SEQ ID NO:38 provided the C-terminal lysine residue may be omitted.

46. The antibody of claim 3, wherein the heavy chain constant region has the amino acid sequence of SEQ ID NO:37 provided the C-terminal lysine residue may be omitted.

47. The antibody of claim 3, wherein the heavy chain constant region has the amino acid sequence of SEQ ID NO:40 provided the C-terminal lysine residue may be omitted.

48. The antibody of claim 3, wherein the light chain constant region has the amino acid sequence of SEQ ID NO:35.

49. The antibody of claim 3, wherein the antibody competes for specific binding to ApoE with 15G8, and wherein the mature heavy chain variable region is fused to a heavy chain constant region and the mature light chain constant region is fused to a light chain constant region.

50. The antibody of claim 3, wherein the antibody binds to the same epitope on ApoE as 15G8, and wherein the mature heavy chain variable region is fused to a heavy chain constant region and the mature light chain constant region is fused to a light chain constant region.

51. An antibody comprising a mature heavy chain variable region having at least 90% sequence identity to SEQ ID NO:17, any variation occurring within the variable region framework of SEQ ID NO:17, and a mature light chain variable region having at least 90% sequence identity to SEQ ID NO:18, any variation occurring within the variable region framework of SEQ ID NO:18, wherein the mature heavy chain variable region comprises the three Kabat CDRs of SEQ ID NO:17 and the mature light chain variable region comprises the three Kabat CDRs of SEQ ID NO:18.

52. The antibody of claim 51, wherein the mature heavy chain variable region has at least 94% sequence identity to SEQ ID NO:17, any variation occurring within the variable region framework of SEQ ID NO:17.

53. The antibody of claim 52, wherein the mature light chain variable region has at least 97% sequence identity to SEQ ID NO:18, any variation occurring within the variable region framework of SEQ ID NO:18.

54. The antibody of claim 51, wherein the mature heavy chain variable region has at least 95% sequence identity to SEQ ID NO:17, any variation occurring within the variable region framework of SEQ ID NO:17 and the mature light chain variable region has at least 95% sequence identity to SEQ ID NO:18, any variation occurring within the variable region framework of SEQ ID NO:18.

55. The antibody of claim 51, wherein the mature light chain variable region has at least 97% sequence identity to SEQ ID NO:18, any variation occurring within the variable region framework of SEQ ID NO:18.

56. The antibody of claim 51, wherein the mature heavy chain variable region has at least 98% sequence identity to SEQ ID NO:17, any variation occurring within the variable region framework of SEQ ID NO:17 and the mature light chain variable region has at least 98% sequence identity to SEQ ID NO:18, any variation occurring within the variable region framework of SEQ ID NO:18.

57. The antibody of claim 51, wherein position L3 (Kabat numbering) is occupied by L.

58. The antibody of claim 51, wherein position L36 (Kabat numbering) is occupied by Y.

59. The antibody of claim 51, wherein position L46 (Kabat numbering) is occupied by L.

60. The antibody of claim 51, wherein position H1 (Kabat numbering) is occupied by E.

61. The antibody of claim 51, wherein position H3 (Kabat numbering) is occupied by K.

62. The antibody of claim 51, wherein position H5 (Kabat numbering) is occupied by V.

63. The antibody of claim 51, wherein position H42 (Kabat numbering) is occupied by E.

64. The antibody of claim 51, wherein position H83 (Kabat numbering) is occupied by R.

65. The antibody of claim 51, wherein the mature heavy chain variable region has an amino acid sequence of SEQ ID NO:11 and the mature light chain variable region has an amino acid sequence of SEQ ID NO:18.

* * * * *

UNITED STATES PATENT AND TRADEMARK OFFICE
CERTIFICATE OF CORRECTION

PATENT NO. : 8,741,298 B2  
APPLICATION NO. : 13/368260  
DATED : June 3, 2014  
INVENTOR(S) : Dale B. Schenk et al.

Page 1 of 1

It is certified that error appears in the above-identified patent and that said Letters Patent is hereby corrected as shown below:

On the Title Page

At (63), delete "(63) Continuation of application No. 61/440,284, filed on Feb. 7, 2011."

At (60), insert -- (60) Provisional application No. 61/440,284, filed on Feb. 7, 2011. --

Signed and Sealed this
Second Day of September, 2014

Michelle K. Lee
*Deputy Director of the United States Patent and Trademark Office*

SEQUENCE LISTING

```
<160> NUMBER OF SEQ ID NOS: 41

<210> SEQ ID NO 1
<211> LENGTH: 299
<212> TYPE: PRT
<213> ORGANISM: Homo sapiens

<400> SEQUENCE: 1

Lys Val Glu Gln Ala Val Glu Thr Glu Pro Glu Pro Glu Leu Arg Gln
 1               5                  10                  15

Gln Thr Glu Trp Gln Ser Gly Gln Arg Trp Glu Leu Ala Leu Gly Arg
```

```
                        20                  25                  30
Phe Trp Asp Tyr Leu Arg Trp Val Gln Thr Leu Ser Glu Gln Val Gln
                35                  40                  45

Glu Glu Leu Leu Ser Ser Gln Val Thr Gln Glu Leu Arg Ala Leu Met
            50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Thr Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
            115                 120                 125

Ser Thr Glu Glu Leu Arg Val Arg Leu Ala Ser His Leu Arg Lys Leu
        130                 135                 140

Arg Lys Arg Leu Leu Arg Asp Pro Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Glu Met Gly Ser Arg
        210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
            275                 280                 285

Thr Ser Ala Ala Pro Val Pro Ser Asp Asn His
        290                 295

<210> SEQ ID NO 2
<211> LENGTH: 299
<212> TYPE: PRT
<213> ORGANISM: Homo sapiens

<400> SEQUENCE: 2

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
                20                  25                  30

Phe Trp Asp Tyr Leu Arg Trp Val Gln Thr Leu Ser Glu Gln Val Gln
            35                  40                  45

Glu Glu Leu Leu Ser Ser Gln Val Thr Gln Glu Leu Arg Ala Leu Met
        50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Thr Ala Gln Ala Arg Leu Gly Ala Asp Met Glu Asp Val Arg
```

```
                  100                 105                 110
Gly Arg Leu Val Gln Tyr Arg Gly Glu Val Gln Ala Met Leu Gly Gln
            115                 120                 125

Ser Thr Glu Glu Leu Arg Val Arg Leu Ala Ser His Leu Arg Lys Leu
        130                 135                 140

Arg Lys Arg Leu Leu Arg Asp Pro Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
    290                 295

<210> SEQ ID NO 3
<211> LENGTH: 272
<212> TYPE: PRT
<213> ORGANISM: Homo sapiens

<400> SEQUENCE: 3

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
    50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Thr Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140

Arg Lys Arg Leu Leu Arg Asp Pro Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
```

```
                    180                 185                 190
Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

<210> SEQ ID NO 4
<211> LENGTH: 272
<212> TYPE: PRT
<213> ORGANISM: Homo sapiens

<400> SEQUENCE: 4

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
    50                  55                  60

Asp Glu Thr Met Lys Glu Leu Lys Ala Tyr Lys Ser Glu Leu Glu Glu
65              70                  75                  80

Gln Leu Thr Pro Val Ala Glu Glu Thr Arg Ala Arg Leu Ser Lys Glu
                85                  90                  95

Leu Gln Thr Ala Gln Ala Arg Leu Gly Ala Asp Met Glu Asp Val Arg
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140

Arg Lys Arg Leu Leu Arg Asp Pro Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

<210> SEQ ID NO 5
<211> LENGTH: 8
<212> TYPE: PRT
```

```
<213> ORGANISM: Artificial Sequence
<220> FEATURE:
<223> OTHER INFORMATION: ApoE 268-272 with artificial CGG linker

<400> SEQUENCE: 5

Cys Gly Gly Leu Val Glu Asp Met
 1               5

<210> SEQ ID NO 6
<211> LENGTH: 11
<212> TYPE: PRT
<213> ORGANISM: Homo sapiens

<400> SEQUENCE: 6

Glu Pro Leu Val Glu Asp Met Gln Arg Gln Trp
 1               5                  10

<210> SEQ ID NO 7
<211> LENGTH: 120
<212> TYPE: PRT
<213> ORGANISM: Homo sapiens

<400> SEQUENCE: 7

Gln Val Gln Leu Gln Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
             20                  25                  30

Gly Met Ser Trp Val Arg Gln Thr Pro Asp Lys Arg Leu Glu Trp Val
         35                  40                  45

Ala Thr Ile Ser Ser Gly Gly Ser Tyr Thr Tyr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg Leu Tyr Tyr Gly Tyr Arg Tyr Tyr Phe Asp Tyr Trp Gly Gln
            100                 105                 110

Gly Thr Met Val Thr Val Ser Ser
        115                 120

<210> SEQ ID NO 8
<211> LENGTH: 112
<212> TYPE: PRT
<213> ORGANISM: Homo sapiens

<400> SEQUENCE: 8

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Leu His Ser
             20                  25                  30

Asp Gly Asn Thr Tyr Leu Leu Trp Phe Leu Gln Arg Pro Gly Gln Ser
         35                  40                  45

Pro Arg Arg Leu Leu Tyr Lys Val Ser Asp Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Trp Thr Phe Gly Gln Gly Thr Lys Val Glu Ile Lys
            100                 105                 110
```

<210> SEQ ID NO 9
<211> LENGTH: 119
<212> TYPE: PRT
<213> ORGANISM: Mus musculus

<400> SEQUENCE: 9

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Phe Tyr
            20                  25                  30

Ala Met Ser Trp Val Arg Gln Thr Pro Glu Lys Arg Leu Glu Trp Val
        35                  40                  45

Ala Ser Leu Ser Arg Gly Gly Ser Thr Tyr Tyr Pro Asp Ser Val Lys
    50                  55                  60

Gly Arg Phe Thr Ile Ser Arg Asp Asn Ala Arg Asn Thr Leu Tyr Leu
65                  70                  75                  80

Gln Met Ser Ser Leu Arg Ser Glu Asp Thr Ala Met Phe Tyr Cys Ala
                85                  90                  95

Arg Glu Gly Ala Thr Ala Leu Tyr Ala Met Asp Tyr Trp Gly Gln Gly
            100                 105                 110

Thr Ser Val Thr Val Ser Ser
        115

<210> SEQ ID NO 10
<211> LENGTH: 112
<212> TYPE: PRT
<213> ORGANISM: Mus musculus

<400> SEQUENCE: 10

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 11
<211> LENGTH: 119
<212> TYPE: PRT
<213> ORGANISM: Artificial Sequence
<220> FEATURE:
<223> OTHER INFORMATION: Hu15G8VHv1 variable region

<400> SEQUENCE: 11

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Phe Tyr
            20                  25                  30

Ala Met Ser Trp Val Arg Gln Thr Pro Glu Lys Arg Leu Glu Trp Val
        35                  40                  45

```
Ala Ser Leu Ser Arg Gly Gly Ser Thr Tyr Tyr Pro Asp Ser Val Lys
     50                  55                  60

Gly Arg Phe Thr Ile Ser Arg Asp Asn Ala Lys Asn Thr Leu Tyr Leu
 65                  70                  75                  80

Gln Met Ser Ser Leu Arg Ser Glu Asp Thr Ala Met Tyr Tyr Cys Ala
                 85                  90                  95

Arg Glu Gly Ala Thr Ala Leu Tyr Ala Met Asp Tyr Trp Gly Gln Gly
            100                 105                 110

Thr Met Val Thr Val Ser Ser
            115
```

<210> SEQ ID NO 12
<211> LENGTH: 357
<212> TYPE: DNA
<213> ORGANISM: Artificial Sequence
<220> FEATURE:
<223> OTHER INFORMATION: Hu15G8VHv1 variable region

<400> SEQUENCE: 12

```
gaggtgaagc tggtggagtc cggcggcggc ctggtgaagc ccggcggctc cctgaagctg      60
tcctgcgccg cctccggctt caccttctcc ttctacgcca tgtcctgggt gcgccagacc     120
cccgagaagc gcctggagtg ggtggcctcc ctgtcccgcg gcggctccac ctactacccc     180
gactccgtga agggccgctt caccatctcc cgcgacaacg ccaagaacac cctgtacctg     240
cagatgtcct ccctgcgctc cgaggacacc gccatgtact actgcgcccg cgagggcgcc     300
accgccctgt acgccatgga ctactggggc cagggcacca tggtgaccgt gtcctcc       357
```

<210> SEQ ID NO 13
<211> LENGTH: 449
<212> TYPE: PRT
<213> ORGANISM: Artificial Sequence
<220> FEATURE:
<223> OTHER INFORMATION: Hu15G8VHv1 + constant region G1m3 allotype

<400> SEQUENCE: 13

```
Glu Val Lys Leu Val Glu Ser Gly Gly Gly Leu Val Lys Pro Gly Gly
  1               5                  10                  15

Ser Leu Lys Leu Ser Cys Ala Ala Ser Gly Phe Thr Phe Ser Phe Tyr
             20                  25                  30

Ala Met Ser Trp Val Arg Gln Thr Pro Glu Lys Arg Leu Glu Trp Val
         35                  40                  45

Ala Ser Leu Ser Arg Gly Gly Ser Thr Tyr Tyr Pro Asp Ser Val Lys
     50                  55                  60

Gly Arg Phe Thr Ile Ser Arg Asp Asn Ala Lys Asn Thr Leu Tyr Leu
 65                  70                  75                  80

Gln Met Ser Ser Leu Arg Ser Glu Asp Thr Ala Met Tyr Tyr Cys Ala
                 85                  90                  95

Arg Glu Gly Ala Thr Ala Leu Tyr Ala Met Asp Tyr Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

Gln Ser Ser Gly Leu Tyr Ser Leu Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 14
<211> LENGTH: 112
<212> TYPE: PRT
<213> ORGANISM: Artificial Sequence
<220> FEATURE:
<223> OTHER INFORMATION: Hu15G8VLv1 variable region

<400> SEQUENCE: 14

Asp Val Leu Met Thr Gln Ser Pro Leu Ser Leu Pro Val Thr Leu Gly
 1               5                  10                  15

Gln Pro Ala Ser Ile Ser Cys Arg Ser Ser Gln Ser Ile Val His Ser
            20                  25                  30

Asn Gly Asn Thr Tyr Leu Gln Trp Tyr Leu Gln Arg Pro Gly Gln Ser
        35                  40                  45

Pro Arg Leu Leu Leu Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly

```
                    85                  90                  95
Ser His Val Pro Trp Thr Phe Gly Gln Gly Thr Lys Val Glu Ile Lys
            100                 105                 110

<210> SEQ ID NO 15
<211> LENGTH: 336
<212> TYPE: DNA
<213> ORGANISM: Artificial Sequence
<220> FEATURE:
<223> OTHER INFORMATION: Hu15G8VLv1 variable region

<400> SEQUENCE: 15
gacgtgctga tgacccagtc ccccctgtcc ctgcccgtga ccctgggcca gcccgcctcc      60
atctcctgcc gctcctccca gtccatcgtg cactccaacg gcaacaccta cctgcagtgg     120
tacctgcagc gccccggcca gtcccccgc ctgctgctgt acaaggtgtc caaccgcttc      180
tccggcgtgc ccgaccgctt ctccggctcc ggctccggca ccgacttcac cctgaagatc     240
tcccgcgtgg aggccgagga cgtgggcgtg tactactgct tccagggctc ccacgtgccc     300
tggaccttcg gccagggcac caaggtggag atcaag                                336

<210> SEQ ID NO 16
<211> LENGTH: 219
<212> TYPE: PRT
<213> ORGANISM: Artificial Sequence
<220> FEATURE:
<223> OTHER INFORMATION: Hu15G8VLv1 + constant region with Arginine

<400> SEQUENCE: 16

Asp Val Leu Met Thr Gln Ser Pro Leu Ser Leu Pro Val Thr Leu Gly
  1               5                   10                  15

Gln Pro Ala Ser Ile Ser Cys Arg Ser Ser Gln Ser Ile Val His Ser
             20                  25                  30

Asn Gly Asn Thr Tyr Leu Gln Trp Tyr Leu Gln Arg Pro Gly Gln Ser
         35                  40                  45

Pro Arg Leu Leu Leu Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 17
<211> LENGTH: 119
<212> TYPE: PRT
<213> ORGANISM: Artificial Sequence
<220> FEATURE:
<223> OTHER INFORMATION: Hu15G8VHv2 variable region

<400> SEQUENCE: 17

Gln Val Gln Leu Gln Glu Ser Gly Gly Gly Leu Val Lys Pro Gly Gly
 1               5                  10                  15

Ser Leu Lys Leu Ser Cys Ala Ala Ser Gly Phe Thr Phe Ser Phe Tyr
            20                  25                  30

Ala Met Ser Trp Val Arg Gln Thr Pro Asp Lys Arg Leu Glu Trp Val
        35                  40                  45

Ala Ser Leu Ser Arg Gly Gly Ser Thr Tyr Tyr Pro Asp Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Lys Ser Glu Asp Thr Ala Met Tyr Tyr Cys Ala
                85                  90                  95

Arg Glu Gly Ala Thr Ala Leu Tyr Ala Met Asp Tyr Trp Gly Gln Gly
            100                 105                 110

Thr Met Val Thr Val Ser Ser
        115

<210> SEQ ID NO 18
<211> LENGTH: 112
<212> TYPE: PRT
<213> ORGANISM: Artificial Sequence
<220> FEATURE:
<223> OTHER INFORMATION: Hu15G8VLv2 variable region

<400> SEQUENCE: 18

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Ile Val His Ser
            20                  25                  30

Asn Gly Asn Thr Tyr Leu Gln Trp Phe Leu Gln Arg Pro Gly Gln Ser
        35                  40                  45

Pro Arg Arg Leu Leu Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 19
<211> LENGTH: 5
<212> TYPE: PRT
<213> ORGANISM: Mus musculus

<400> SEQUENCE: 19

Phe Tyr Ala Met Ser
 1               5

<210> SEQ ID NO 20
<211> LENGTH: 16
<212> TYPE: PRT
<213> ORGANISM: Mus musculus
```

```
<400> SEQUENCE: 20

Ser Leu Ser Arg Gly Gly Ser Thr Tyr Tyr Pro Asp Ser Val Lys Gly
1               5                   10                  15

<210> SEQ ID NO 21
<211> LENGTH: 11
<212> TYPE: PRT
<213> ORGANISM: Mus musculus

<400> SEQUENCE: 21

Glu Gly Ala Thr Ala Leu Tyr Ala Met Asp Tyr
1               5                   10

<210> SEQ ID NO 22
<211> LENGTH: 16
<212> TYPE: PRT
<213> ORGANISM: Mus musculus

<400> SEQUENCE: 22

Arg Ser Ser Gln Ser Ile Val His Ser Asn Gly Asn Thr Tyr Leu Gln
1               5                   10                  15

<210> SEQ ID NO 23
<211> LENGTH: 7
<212> TYPE: PRT
<213> ORGANISM: Mus musculus

<400> SEQUENCE: 23

Lys Val Ser Asn Arg Phe Ser
1               5

<210> SEQ ID NO 24
<211> LENGTH: 9
<212> TYPE: PRT
<213> ORGANISM: Mus musculus

<400> SEQUENCE: 24

Phe Gln Gly Ser His Val Pro Trp Thr
1               5

<210> SEQ ID NO 25
<211> LENGTH: 19
<212> TYPE: PRT
<213> ORGANISM: Mus musculus

<400> SEQUENCE: 25

Met Asp Ser Arg Leu Asn Leu Val Phe Leu Val Leu Val Leu Lys Gly
1               5                   10                  15

Val Gln Cys

<210> SEQ ID NO 26
<211> LENGTH: 19
<212> TYPE: PRT
<213> ORGANISM: Mus musculus

<400> SEQUENCE: 26

Met Asp Phe Gly Phe Ser Leu Val Phe Leu Val Leu Val Leu Lys Gly
1               5                   10                  15

Val Gln Cys

<210> SEQ ID NO 27
<211> LENGTH: 19
<212> TYPE: PRT
```

-continued

<213> ORGANISM: Mus musculus

<400> SEQUENCE: 27

Met Asp Phe Gly Leu Ser Leu Val Phe Leu Val Leu Val Leu Lys Gly
1               5                   10                  15

Val Gln Cys

<210> SEQ ID NO 28
<211> LENGTH: 19
<212> TYPE: PRT
<213> ORGANISM: Mus musculus

<400> SEQUENCE: 28

Met Lys Leu Pro Val Arg Leu Leu Val Leu Met Phe Trp Ile Pro Ala
1               5                   10                  15

Ser Ser Ser

<210> SEQ ID NO 29
<211> LENGTH: 57
<212> TYPE: DNA
<213> ORGANISM: Artificial Sequence
<220> FEATURE:
<223> OTHER INFORMATION: nucleotide sequence encoding Hu15G8VH signal
      peptide v1

<400> SEQUENCE: 29
atggagttcg gcctgtcctg gctgttcctg gtggccatcc tgaagggcgt gcagtgc         57

<210> SEQ ID NO 30
<211> LENGTH: 19
<212> TYPE: PRT
<213> ORGANISM: Artificial Sequence
<220> FEATURE:
<223> OTHER INFORMATION: Hu15G8VH signal peptide v1

<400> SEQUENCE: 30

Met Glu Phe Gly Leu Ser Trp Leu Phe Leu Val Ala Ile Leu Lys Gly
1               5                   10                  15

Val Gln Cys

<210> SEQ ID NO 31
<211> LENGTH: 57
<212> TYPE: DNA
<213> ORGANISM: Artificial Sequence
<220> FEATURE:
<223> OTHER INFORMATION: nucleotide sequence encoding Hu15G8VH signal
      peptide v2

<400> SEQUENCE: 31
atggactgga cctggagcat ccttttcttg gtggcagcag caacaggtgc ccactcc         57

<210> SEQ ID NO 32
<211> LENGTH: 19
<212> TYPE: PRT
<213> ORGANISM: Artificial Sequence
<220> FEATURE:
<223> OTHER INFORMATION: Hu15G8VH signal peptide v2

<400> SEQUENCE: 32

Met Asp Trp Thr Trp Ser Ile Leu Phe Leu Val Ala Ala Ala Thr Gly
1               5                   10                  15

Ala His Ser

<210> SEQ ID NO 33

-continued

```
<211> LENGTH: 66
<212> TYPE: DNA
<213> ORGANISM: Artificial Sequence
<220> FEATURE:
<223> OTHER INFORMATION: nucleotide sequence encoding Hu15G8VL signal
      peptide

<400> SEQUENCE: 33
atggacatgc gcgtgcccgc ccagctgctg ggcctgctga tgctgtgggt gtccggctcc    60
tccggc                                                               66

<210> SEQ ID NO 34
<211> LENGTH: 22
<212> TYPE: PRT
<213> ORGANISM: Artificial Sequence
<220> FEATURE:
<223> OTHER INFORMATION: Hu15G8VL signal peptide

<400> SEQUENCE: 34

Met Asp Met Arg Val Pro Ala Gln Leu Leu Gly Leu Leu Met Leu Trp
 1               5                  10                  15

Val Ser Gly Ser Ser Gly
            20

<210> SEQ ID NO 35
<211> LENGTH: 107
<212> TYPE: PRT
<213> ORGANISM: Homo sapiens

<400> SEQUENCE: 35

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 36
<211> LENGTH: 106
<212> TYPE: PRT
<213> ORGANISM: Artificial Sequence
<220> FEATURE:
<223> OTHER INFORMATION: light chain kappa constant region (without
      5' R)

<400> SEQUENCE: 36

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60
```

```
Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
                100                 105

<210> SEQ ID NO 37
<211> LENGTH: 330
<212> TYPE: PRT
<213> ORGANISM: Homo sapiens

<400> SEQUENCE: 37

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 38
<211> LENGTH: 330
<212> TYPE: PRT
<213> ORGANISM: Homo sapiens

<400> SEQUENCE: 38

```
Ala Ser Thr Lys Gly Pro Ser Val Phe Pro Leu Ala Pro Ser Ser Lys
  1               5                  10                  15
Ser Thr Ser Gly Gly Thr Ala Ala Leu Gly Cys Leu Val Lys Asp Tyr
                 20                  25                  30
Phe Pro Glu Pro Val Thr Val Ser Trp Asn Ser Gly Ala Leu Thr Ser
             35                  40                  45
Gly Val His Thr Phe Pro Ala Val Leu Gln Ser Ser Gly Leu Tyr Ser
         50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 39
<211> LENGTH: 330
<212> TYPE: PRT
<213> ORGANISM: Homo sapiens

<400> SEQUENCE: 39

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                   70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
     130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                 165                 170                 175

Glu Gln Tyr Asn Ser Thr Tyr Arg Val Val Ser Val Leu Thr Val Leu
             180                 185                 190

His Gln Asp Trp Leu Asn Gly Lys Glu Tyr Lys Cys Lys Val Ser Asn
         195                 200                 205

Lys Ala Leu Pro Ala Pro Ile Glu Lys Thr Ile Ser Lys Ala Lys Gly
     210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                 245                 250                 255

Pro Ser Asp Ile Ala Val Glu Trp Glu Ser Asn Gly Gln Pro Glu Asn
             260                 265                 270

Asn Tyr Lys Thr Thr Pro Pro Val Leu Asp Ser Asp Gly Ser Phe Phe
         275                 280                 285

Leu Tyr Ser Lys Leu Thr Val Asp Lys Ser Arg Trp Gln Gln Gly Asn
     290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                 325                 330

<210> SEQ ID NO 40
<211> LENGTH: 326
<212> TYPE: PRT
<213> ORGANISM: Homo sapiens

<400> SEQUENCE: 40

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45
```

```
Gly Val His Thr Phe Pro Ala Val Leu Gln Ser Ser Gly Leu Tyr Ser
    50              55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
            115                 120                 125
Thr Leu Met Ile Ser Arg Thr Pro Glu Val Thr Cys Val Val Val Asp
            130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
                180                 185                 190
Leu Asn Gly Lys Glu Tyr Lys Cys Lys Val Ser Asn Lys Gly Leu Pro
            195                 200                 205
Ala Pro Ile Glu Lys Thr Ile Ser Lys Thr Lys Gly Gln Pro Arg Glu
            210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
                260                 265                 270
Thr Pro Pro Met Leu Asp Ser Asp Gly Ser Phe Phe Leu Tyr Ser Lys
                275                 280                 285
Leu Thr Val Asp Lys Ser Arg Trp Gln Gln Gly Asn Val Phe Ser Cys
            290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 41
<211> LENGTH: 5
<212> TYPE: PRT
<213> ORGANISM: Artificial Sequence
<220> FEATURE:
<223> OTHER INFORMATION: ApoE4 (268-272)

<400> SEQUENCE: 41

Leu Val Glu Asp Met
1               5
```